(12) United States Patent
Ashley et al.

(10) Patent No.: US 10,016,411 B2
(45) Date of Patent: Jul. 10, 2018

(54) SLOW-RELEASE CONJUGATES OF SN-38

(71) Applicant: ProLynx LLC, San Francisco, CA (US)

(72) Inventors: Gary W. Ashley, Alameda, CA (US); Eric L. Schneider, Oakland, CA (US)

(73) Assignee: ProLynx LLC, San Francisco, CA (US)

( * ) Notice: Subject to any disclaimer, the term of this patent is extended or adjusted under 35 U.S.C. 154(b) by 0 days.

(21) Appl. No.: 15/026,579

(22) PCT Filed: Oct. 3, 2014

(86) PCT No.: PCT/US2014/059146
§ 371 (c)(1),
(2) Date: Mar. 31, 2016

(87) PCT Pub. No.: WO2015/051307
PCT Pub. Date: Apr. 9, 2015

(65) Prior Publication Data
US 2016/0243106 A1    Aug. 25, 2016

Related U.S. Application Data

(60) Provisional application No. 61/887,111, filed on Oct. 4, 2013.

(51) Int. Cl.
| | |
|---|---|
| *A61K 31/4745* | (2006.01) |
| *A61K 47/48* | (2006.01) |
| *C07D 457/00* | (2006.01) |
| *C08G 83/00* | (2006.01) |
| *C07D 519/00* | (2006.01) |
| *A61K 47/10* | (2017.01) |
| *A61K 47/20* | (2006.01) |
| *C07D 491/22* | (2006.01) |
| *C08G 65/48* | (2006.01) |

(52) U.S. Cl.
CPC .......... *A61K 31/4745* (2013.01); *A61K 47/10* (2013.01); *A61K 47/20* (2013.01); *A61K 47/48215* (2013.01); *C07D 457/00* (2013.01); *C07D 491/22* (2013.01); *C07D 519/00* (2013.01); *C08G 65/48* (2013.01); *C08G 83/002* (2013.01)

(58) Field of Classification Search
CPC .. C07D 471/00; C07D 491/00; C07D 498/00; C07D 513/00; A61K 31/44
USPC ............................................ 546/48; 514/280
See application file for complete search history.

(56) References Cited

U.S. PATENT DOCUMENTS

| | | |
|---|---|---|
| 8,299,089 B2 | 10/2012 | Zhao et al. |
| 2004/0176270 A1 * | 9/2004 | Chen ................ A61K 47/48215 530/402 |
| 2006/0067910 A1 | 3/2006 | Kitagawa et al. |
| 2010/0305149 A1 | 12/2010 | Yurkovetskiy et al. |

FOREIGN PATENT DOCUMENTS

| | | | |
|---|---|---|---|
| WO | WO-2004/039869 | 5/2004 | |
| WO | WO 2005007136 A1 * | 1/2005 | ................ A61K 9/19 |
| WO | WO 2005028539 A2 * | 3/2005 | ....... A61K 47/48176 |
| WO | WO-2011/140393 | 11/2011 | |
| WO | WO 2011140393 A1 * | 11/2011 | ........... A61K 9/0019 |
| WO | WO-2011140393 A1 * | 11/2011 | ........... A61K 9/0019 |

* cited by examiner

*Primary Examiner* — Timothy P Thomas
*Assistant Examiner* — George W Kosturko
(74) *Attorney, Agent, or Firm* — Morrison & Foerster LLP

(57) ABSTRACT

Conjugates of SN-38 that provide optimal drug release rates and minimize the formation of the corresponding glucuronate are described. The conjugates release SN-38 from a polyethylene glycol through a β-elimination mechanism.

4 Claims, 7 Drawing Sheets

SLOW-RELEASE CONJUGATES OF SN-38

CROSS-REFERENCE TO RELATED APPLICATIONS

This application is the national phase of PCT application PCT/US2014/059146 having an international filing date of 3 Oct. 2014, which claims benefit of U.S. Provisional Application Serial No. 61/887,111 filed 4 Oct. 2013. The contents of the above patent applications are incorporated by reference herein in their entirety.

TECHNICAL FIELD

The invention relates to slow-release systems for an anticancer drug, SN-38.

BACKGROUND ART

The camptothecin analog SN-38 (7-ethyl-10-hydroxycamptothecin) is an active metabolite of the antitumor drug irinotecan. It is ~1000× more active than irinotecan, yet has not been therapeutically useful due to extremely poor aqueous solubility (17 uM) and rapid clearance.

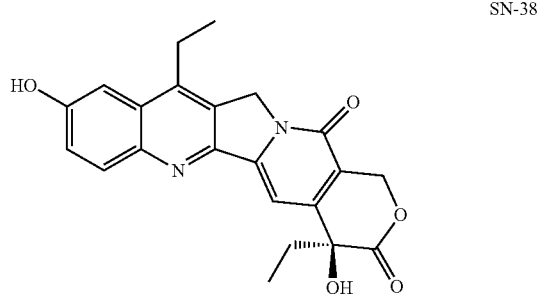 [SMILES: CCc1c2c(nc3ccc(O)cc13)-c1cc3c(c(=O)n1C2)COC(=O)[C@]3(O)CC]

SN-38

Irinotecan itself is used clinically and has shown activity in leukemia, lymphoma, colorectal, lung, ovarian, cervical, pancreatic, stomach, and breast cancers. Several studies have indicated that the camptothecins in general owe their antitumor effects to inhibition of topoisomerase I, and that efficacy is related to maintaining inhibition of this enzyme for prolonged periods ("time over target"). In order to maintain efficacious levels of camptothecins for a sufficient time, it is typically required that fairly high doses of drug be administered to counter the relatively rapid clearance rate of the drug from the system. This results in high maximal drug concentrations ($C_{max}$) at early times after administration, which is thought to result in toxicities such as the life-threatening diarrhea that is the dose-limiting toxicity for irinotecan. Given the high potency of SN-38, it would be desirable to provide the drug as a prolonged infusion at a steady-state concentration sufficient for inhibition of topoisomerase I but lower than the toxic concentration. Clinical trials using prolonged infusion of irinotecan via pumps have corroborated this hypothesis, yet this is not a feasible therapeutic strategy for SN-38 due to poor solubility in dosing formulations.

Irinotecan is converted into SN-38 by hepatic carboxyesterase, and then metabolized by hepatic UGT1A to its 10-glucuronide, SN-38G. Glucuronidation facilitates biliary excretion and intestinal bacterial glucuronidase causes reconversion of SN-38G to SN-38. Unless intestinal UGT1A converts the drug back to the inert SN-38G, the SN-38 can cause toxic effects on the intestine. Thus, SN-38G may act both as the source of the toxic SN-38 and a protection against the severe diarrhea caused by SN-38. In general, high levels of SN-38 result in increased glucuronidation to SN-38G, increased excretion of SN-38G into the intestine, and bacterial deglucuronidation that results in gastrointestinal toxicity.

Slow release of SN-38 from a soluble, long-lived circulating conjugate rather than from a prodrug such as irinotecan would seem to provide a solution to these problems, and various conjugation strategies have been applied to SN-38. Conjugation to poly(ethylene glycol) (PEG) via an oxygen-20 glycinate ester (U.S. Pat. No. 8,299,089) provides a relatively aqueous-soluble conjugate that releases free SN-38 relatively rapidly ($t_{1/2}$=12 h) due to ester hydrolysis. Another ester-linking chemistry to a polyol polymer with fast release of SN-38 has been disclosed (US Patent Publication 2010/0305149 A1). Conjugation to a polyglutamate-PEG block copolymer via ester linkages to oxygen-10 provides a micellar conjugate that again releases free SN-38 by ester hydrolysis (PCT Publication WO2004/039869). Due to the instability of esters in aqueous media, possibly accelerated by esterases in plasma, such ester-based conjugation strategies for SN-38 are not appropriate to support low-dose, long-term exposure to SN-38, and levels of SN-38 typically fall below the efficacious level between dosings. The conjugates are typically administered at high levels, giving high maximal concentrations of SN-38 and resulting in formation of high levels of SN-38G.

PEG-SN-38 conjugates having more controlled release rates have been disclosed in PCT Publication WO2011/140393. These conjugates release SN-38 through a beta-elimination mechanism, with rates controllable over a wide range through selection of the appropriate linker. Coupling a macromolecule to this drug was through a condensation product of azido with a cyclic alkyne resulting in a relatively insoluble conjugate. The subgenus claimed herein has improved solubility due to the presence of a simple amide linkage, and is stable in vitro in buffer at room temperature. We have now unexpectedly found that through appropriate selection of the release rate the in vivo formation of SN-38G may be reduced while simultaneously providing a long-term exposure to active SN-38. The present invention provides conjugates that are designed to release free SN-38 through a non-enzymatic beta-elimination mechanism at rates that enable low-dose, long-term exposure regimens for SN-38 and which further reduce the amount of SN-38G formed during administration.

DISCLOSURE OF THE INVENTION

The present invention provides conjugates that are designed to release free SN-38 through a non-enzymatic beta-elimination mechanism at slow rates that enable low-dose, long-term exposure regimens for SN-38 and which further reduce the amount of SN-38G formed during administration. Also provided are methods for producing the conjugates and methods for their use in the treatment of diseases and conditions characterized by cellular hyperproliferation.

Thus in one aspect, the invention provides conjugates having formula (I)

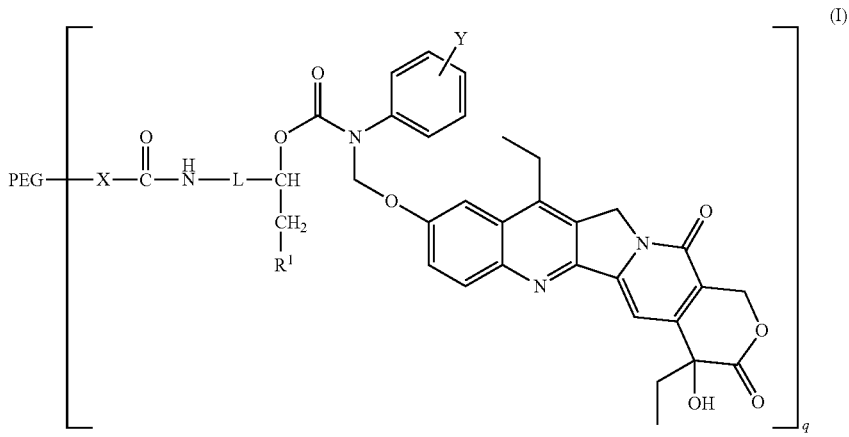

wherein PEG is a polyethylene glycol of average molecular weight between 20,000 and 60,000 Da which is linear or branched and when q is 2-8, multi-armed;
q=1-8;
X is O, NH, $(CH_2)_m$, $OC(=O)(CH_2)_m$, or $NHC(=O)(CH_2)_m$ wherein m=1-6;
$R^1$ is CN or $SO_2NR^2{}_2$ wherein each $R^2$ is independently alkyl, aryl, heteroaryl, alkylalkenyl, alkylaryl, or alkylheteroaryl, each optionally substituted, or taken together can form a ring;
$Y=COR^3$ or $SO_2R^3$ wherein $R^3$=OH, alkoxy, or $NR^4{}_2$, wherein each $R^4$ is independently alkyl, substituted alkyl, or taken together can form a ring; and
L is $(CH_2)_r$ or $(CH_2CH_2O)_p(CH_2)_r$, wherein r=1-10 and p=1-10.

In a second aspect, the invention provides methods for the preparation of conjugates of formula (I) as well as intermediates thereto.

In a third aspect, the invention provides methods for the slow release of SN-38 using conjugates of formula (I).

In a fourth aspect, the invention provides methods for minimizing the amount of SN-38 glucuronide formed upon administration of SN-38 by control of the release rate of SN-38 from a conjugate.

In a fifth aspect, the invention relates to a formulation that solubilizes SN-38 comprising PEG and DMSO and methods for use thereof.

MODES OF CARRYING OUT THE INVENTION

Figure 1:
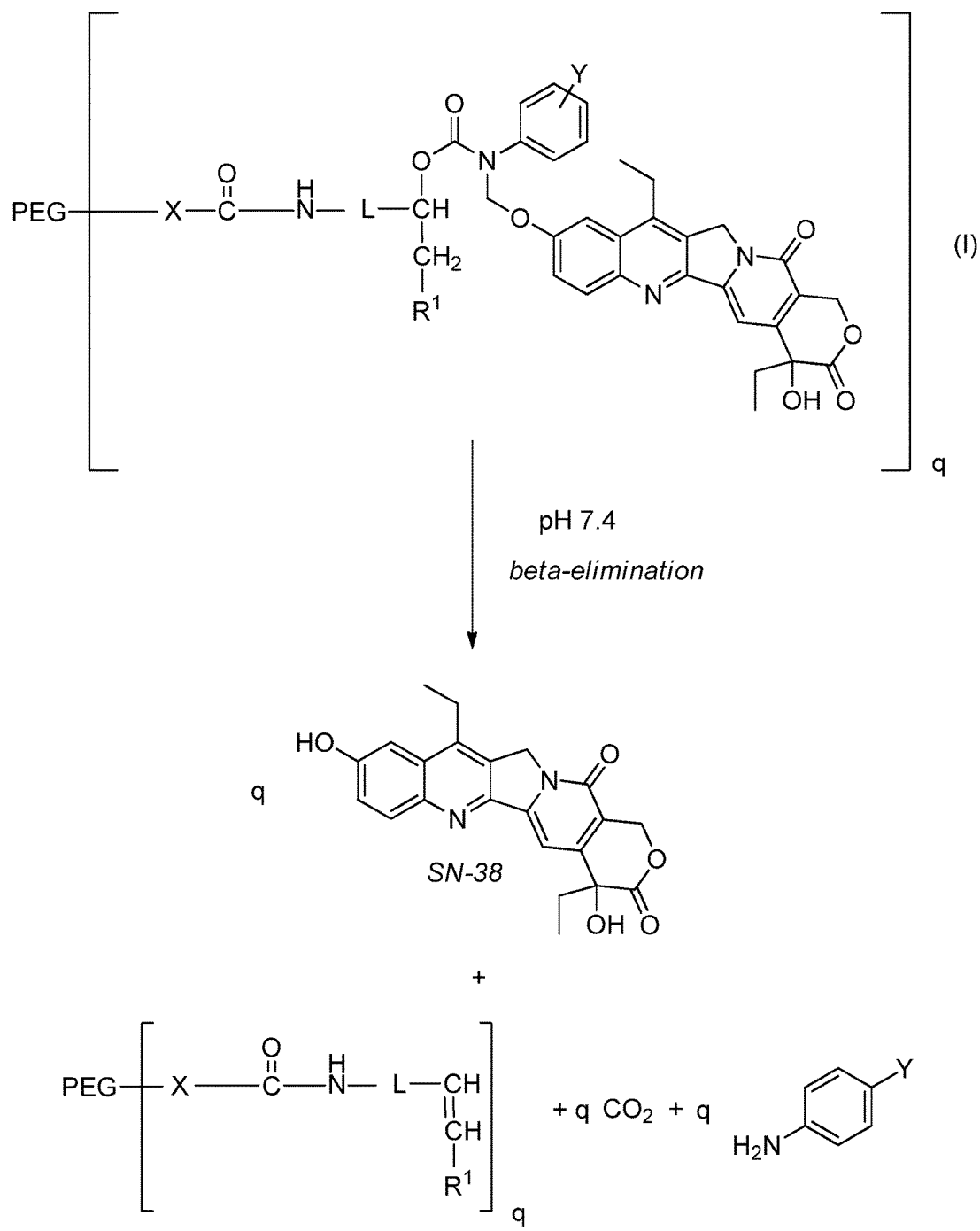
FIG. 1 illustrates the release of free SN-38 from conjugates of the invention.

In one aspect, the invention provides conjugates having formula (I)

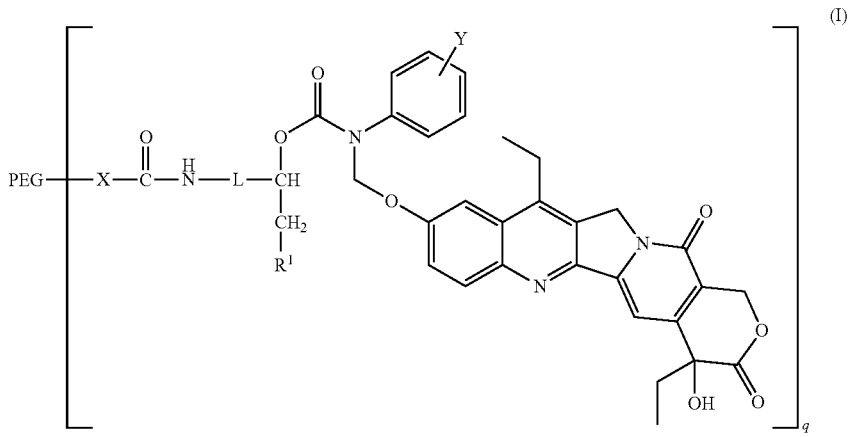

wherein PEG is a linear or branched and, when q is 2-8, multi-armed, polyethylene glycol of average molecular weight between 20,000 and 60,000 Da;

q=1-8;

X is O, NH, $(CH_2)_m$, $OC(=O)(CH_2)_m$, or $NHC(=O)(CH_2)_m$ wherein m=1-6;

$R^1$ is CN or $SO_2NR^2{}_2$ wherein each $R^2$ is independently alkyl, aryl, heteroaryl, alkylalkenyl, alkylaryl, or alkylheteroaryl, each optionally substituted, or taken together can form a ring;

$Y=COR^3$ or $SO_2R^3$ and $R^3$=OH, alkoxy, or $NR^4{}_2$, wherein each $R^4$ is independently alkyl, substituted alkyl, or taken together can form a ring; and L is $(CH_2)_r$ or $(CH_2CH_2O)_p(CH_2)_r$, wherein r =1-10 and p=1-10.

The term "alkyl" is defined as a linear, branched, or cyclic saturated hydrocarbon group of 1-8 carbons, or in some embodiments 1-6 or 1-4 carbon atoms.

The term "alkenyl" is defined as a non-aromatic linear, branched, or cyclic unsaturated hydrocarbon of 1-6 or 1-4C with one or more carbon-carbon double bonds.

The term "alkynyl" is defined as a non-aromatic linear, branched, or cyclic unsaturated hydrocarbon of 1-6 or 1-4C with one or more carbon-carbon triple bonds.

The term "alkoxy" is defined as an alkyl group bonded to oxygen, including methoxy, ethoxy, isopropoxy, cyclopropoxy, cyclobutoxy, and similar.

The term "aryl" is defined as an aromatic hydrocarbon group of 6-18 carbons, preferably 6-10 carbons, including groups such as phenyl, naphthyl, and anthracenyl. The term "heteroaryl" is defined as aromatic rings comprising 3-15 carbons containing at least one N, O or S atom, preferably 3-7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and similar.

The term "halogen" includes bromo, fluoro, chloro and iodo.

Where groups are "optionally substituted" the substituents include 1-3 substituents that are the same or different and may include halogen, amino, hydroxyl, and sulfhydryl, as well as substituents that contain carboxyl groups either as esters, amides, or as free carboxyl groups. This list is not intended to be all-encompassing, and any noninterfering substituent may be included among those that are optionally present.

As used herein "a", "an", etc., are intended to mean one or more than one unless otherwise indicated. Further, where ranges of integers are provided, all intermediate integers are intended to be included as if specifically set forth.

The PEG may be a linear, branched, or multi-arm poly (ethylene glycol) of average molecular weight between 20,000 and 60,000 (i.e., comprising from approximately 400 to approximately 1500 ethylene oxide units) or 30,000-50,000, wherein at least one polymer end may be terminated with a carboxylate functionality. These PEGs are commercially available, for example through NOF and Jenkem Technologies, as derivatives where the C=O group is activated for reaction with amines as N-hydroxysuccinimide or nitrophenyl esters or N-hydroxysuccinimidyl or nitrophenyl carbonates. These high-molecular weight PEGs are comprised of a Gaussian distribution of molecular weights (i.e., are polydisperse), and thus comprise a distribution of the number of ethylene oxide units; they are described by an average molecular weight that is herein intended to encompass the distribution of molecular weights and ethylene oxide units commonly found in industrially-supplied materials having the described average molecular weight. Typical polydispersity indices (PDI) for 4-arm PEGs are less than or equal to 1.1, and are calculated as $PDI=M_w/M_m$, where $M_w$=weight-average molar mass calculated as $\Sigma M_i^2 N_i/\Sigma M_i N_i$ and $M_m$=number-average molar mass calculated as $\Sigma M_i N_i/\Sigma N_i$, wherein M is the molecular weight of species i and N is the number of species i in the sample. PDI may be measured by techniques known in the art such as gel permeation chromatography HPLC or mass spectrometry (see, for example, US Patent Publication 2010/0126866 A1). The multi-arm PEGs may be formed starting from a variety of core units, including pentaerythritol, hexaglycerol, and tripentaerythritol,

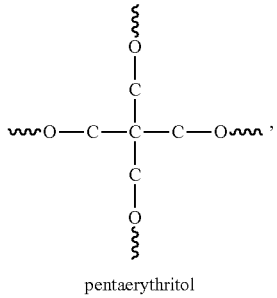

pentaerythritol

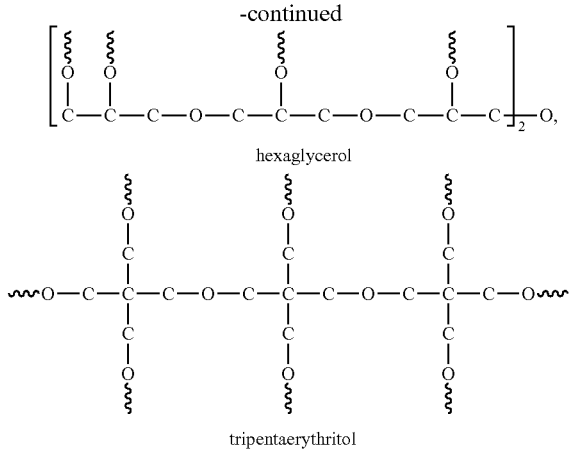

hexaglycerol tripentaerythritol to provide a variety of configurations and total number of arms. At least one arm of the PEG is terminated with a carboxylate functionality through connecting group X to allow attachment of the linker-SN-38. X serves to attach the carboxylate functionality to the PEG, and thus may be any of the typical connector groups including O, NH, $(CH_2)_m$, $OC(=O)(CH_2)_m$, or $NHC(=O)(CH_2)_m$ wherein m=1-6. In certain embodiments of the invention, X is O, NH, $(CH_2)_m$, or $NHC(=O)(CH_2)_m$. In one embodiment of the invention, X is $(CH_2)_m$.

In certain specific embodiments of the invention, the PEG has an average molecular weight of 40,000±4,000 Da (i.e., comprising from approximately 800-1000 total ethylene oxide units). In one embodiment, the PEG is a 4-arm polymer having a pentaerythritol core and an average molecular weight of 40,000±4,000 Da, wherein each arm thus comprises 225±25 ethylene oxide units on average and is terminated by a carboxylate group, and having the formula (III).

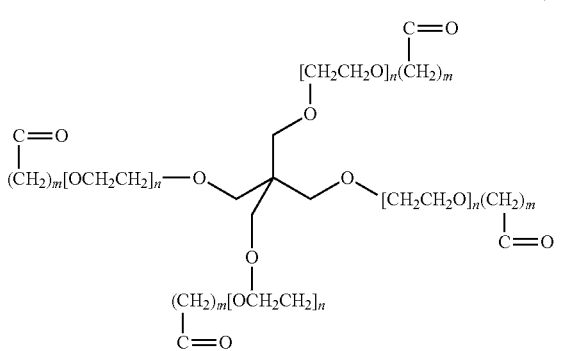

(III)

wherein n=200-250 and m=1-6. While related conjugates have been previously disclosed in PCT Publication WO2011/140393, we have unexpectedly found that connection of the PEG to the linker-SN-38 through a more hydrophilic amide linkage provides conjugates with improved solubility and viscosity properties over the previously disclosed conjugates wherein the PEG was connected via a 1,3-dipolar cycloaddition between an azide and a dibenzoazacyclooctyne (DBCO or DIBOC).

L is a connecting group having the formula $(CH_2)_r$ or $(CH_2CH_2O)_p(CH_2)_r$, wherein r=1-10 and p=1-10.

$R^1$ is CN or $SO_2NR^2{}_2$, wherein each $R^2$ is independently alkyl, aryl, heteroaryl, alkylalkenyl, alkylaryl, or alkylheteroaryl, each optionally substituted, or taken together can form a ring. In some embodiments, each $R^2$ is independently alkyl. $R^1$ controls the rate of release of SN-38 from the conjugate, as described in PCT publication WO2011/140393 and PCT Application PCT/US 12/54293, which are incorporated herein by reference. To support low-dose, long-term exposure regimens the rate of SN-38 release from the conjugates should be such that the in vivo half-life of release is between approximately 100 and approximately 1000 hours, preferably between approximately 300 and approximately 800 hours, and most preferably approximately 400 to 500 hours. It is noted that in vivo release rates may be up to approximately 3× faster than the corresponding in vitro release rates measured at pH 7.4, 37° C. In certain embodiments, $R^1$ is CN. In this embodiment, the in vitro and in vivo (rat) half-life of release has been measured as 400 h. In certain other embodiments, $R^1$ is $SO_2NR^2{}_2$. In certain specific embodiments, $R^1$ is $SO_2NR^2{}_2$ wherein each $R^2$ is independently methyl, ethyl, allyl, benzyl, 2-methoxyethyl, or 3-methoxypropyl, or $NR^2{}_2$ forms morpholino, 2,3-dihydroindolyl, or 1,2,3,4-tetrahydroquinolyl.

Y is an electron-withdrawing substituent that stabilizes the conjugate against premature release. In certain embodiments, Y is $COR^3$ or $SO_2R^3$, wherein $R^3$=OH, $OR^4$, or $NR^4{}_2$, wherein each $R^4$ is independently alkyl, substituted alkyl, or both $R^4$ taken together can form a ring. In some embodiments, Y is in the para position. Y serves to stabilize the N—$CH_2$—O linkage to SN-38 thus minimizing the rate of spontaneous cleavage of drug from the conjugate. In certain embodiments, Y is $CONR^4{}_2$, and in certain specific embodiments Y is $CON(CH_2CH_3)_2$, $CON(CH_2CH_2)_2O$, or $SO_2N(CH_2CH_2)_2O$ where $(CH_2CH_2)_2O$ combined with N is morpholino. The p-aminobenzoates and p-aminosulfonamides resulting from beta-elimination and release of SN-38 are generally considered to have low toxicity.

In a specific embodiment of the invention, a conjugate of formula (I) having the structure (II) is provided (II)
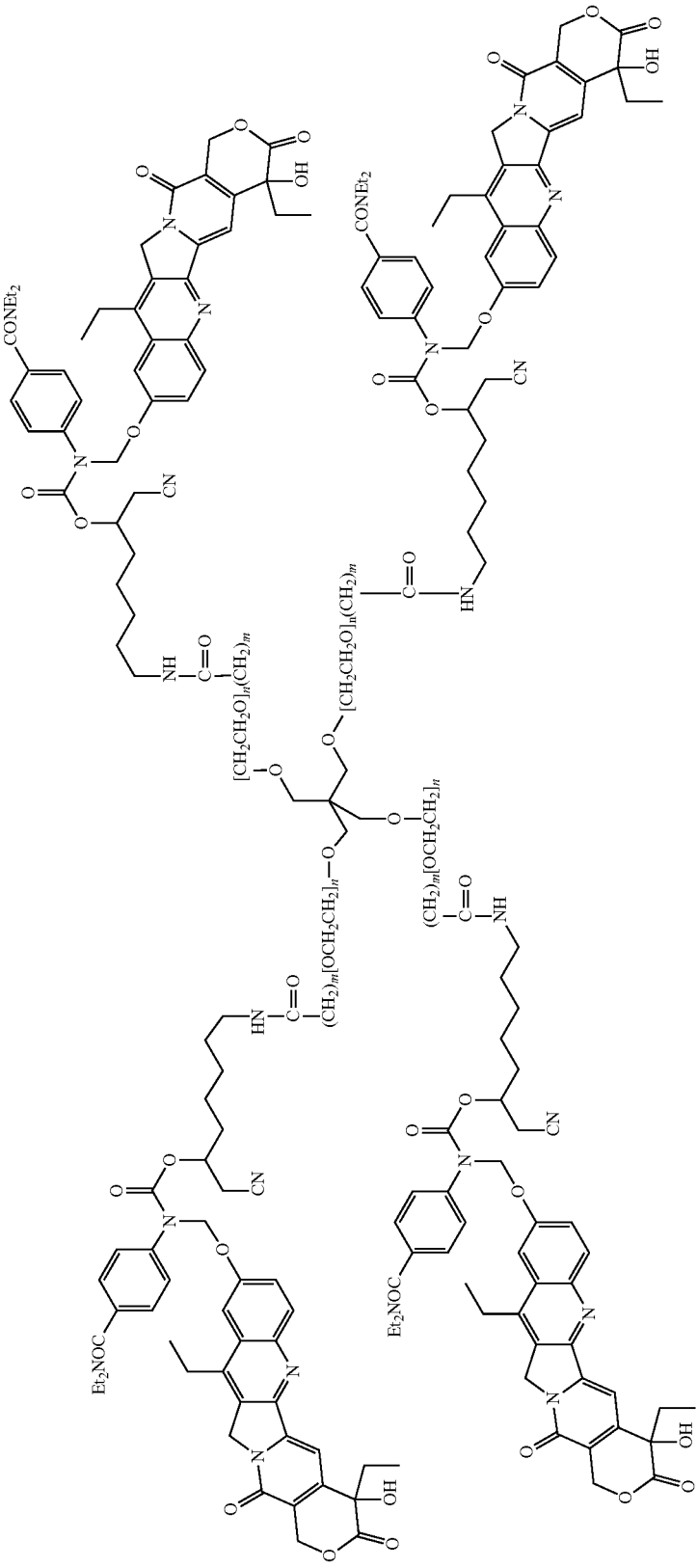

wherein m=1-6 and n=100-375 (i.e., a PEG of average molecular weight between 20,000 and 60,000 Da, or 30,000-50,000 Da). In a more specific embodiment of the invention, a conjugate having formula (II) is provided wherein m=1-3. In an even more specific embodiment of the invention, m=1 and n=200-250 or ~225 such that the average PEG molecular weight is about 40,000.

Figure 2:
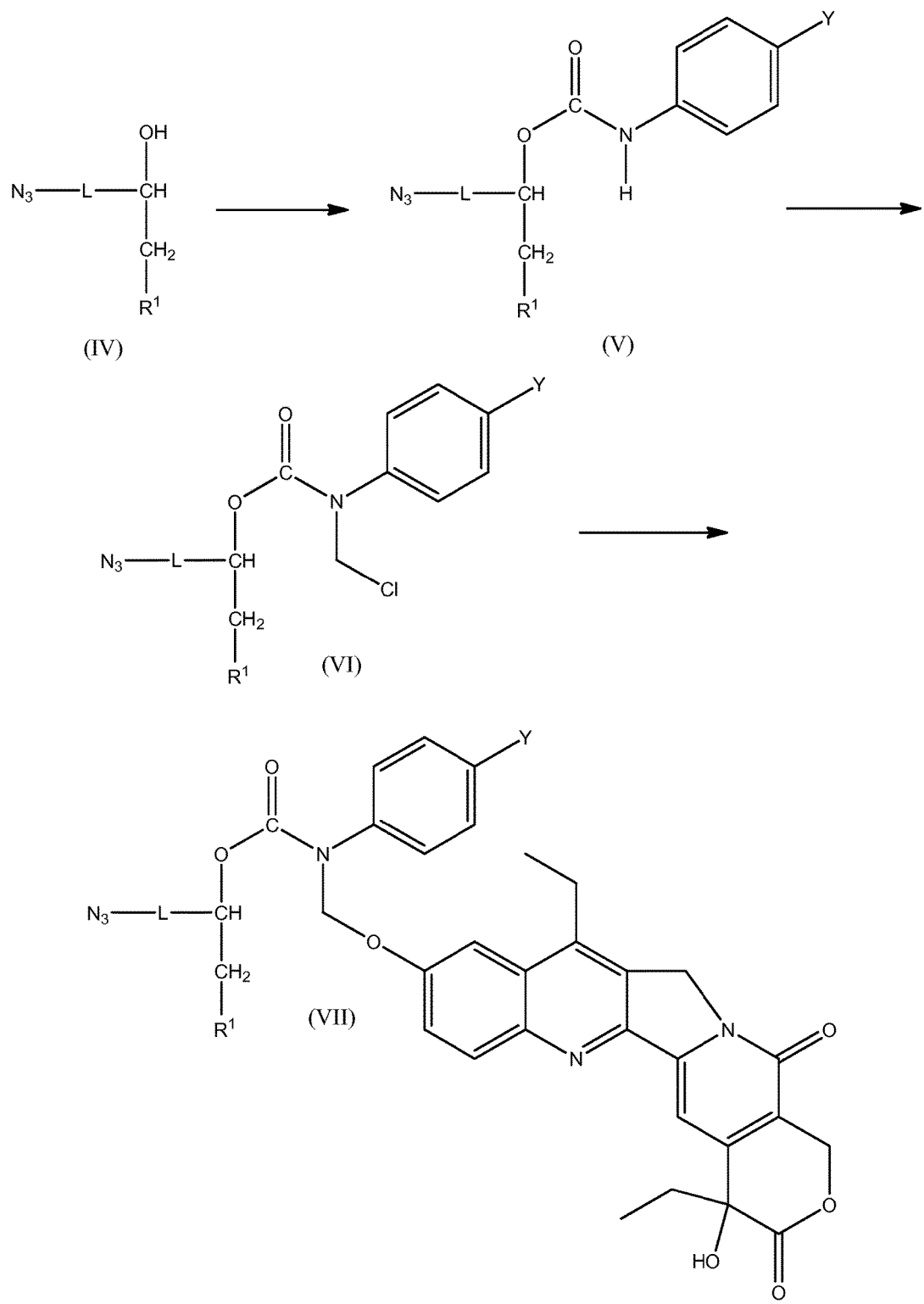
FIG. 2 illustrates one method for the preparation of azido-linker-SN-38 (VII) intermediates of the invention.

In another aspect of the invention, methods for the preparation of the conjugates of formula (I) are given. One method for the preparation of azido-linker-SN-38 intermediate, previously disclosed in PCT Publication WO2011/140393, is illustrated in FIG. 2. Thus, an azido alcohol (IV) is converted into carbamate (V), for example by intermediate conversion to the chloroformate using phosgene or a phosgene equivalent such as triphosgene in the presence of a mild base such as pyridine, followed by reaction with the aniline $NH_2$—$C_6H_4$—Y. Alternately, (V) may be formed directly by treatment of (IV) with isocyanate OCN—$C_6H_4$—Y. The carbamate (V) is then N-chloromethylated using a modification of the method disclosed by Majumdar ("N-Alkyl-N-alkyloxycarbonylaminomethyl (NANAO-CAM) prodrugs of carboxylic acid containing drugs," *Bioorg Med Chem Letts* (2007) 17:1447-1450), wherein the carbamate (V) and paraformaldehyde are contacted in a mixture of chlorotrimethylsilane and an inert solvent such as tetrahydrofuran, 1,2-dichloroethane, dioxane, or toluene. In a preferred embodiment, the inert solvent is toluene. The catalyst chlorotrimethylsilane is present in 1-10-fold molar excess over (V), preferably in 4-fold molar excess. The reaction may be performed at temperatures between 20 and 100° C., preferably between 40 and 60° C., and most preferably at 50° C., under inert atmosphere, and the reaction progress may be monitored by conversion of the reactive N-(chloromethyl)carbamate (VI) into a stable species, for example by dilution of an aliquot of the reaction mixture into ethanol containing sufficient trialkylamine base to neutralize the chloro-trimethylsilane followed by HPLC analysis of the resulting N-(ethoxymethyl)-carbamate.

SN-38 is alkylated on the phenolic OH by N-(chloromethyl)carbamate (VI) to produce the azido-linker-SN-38 (VII), illustrated in FIG. 2. A variety of bases may be used to deprotonate the phenol and thus effect the alkylation, including alkoxides such as potassium tert-butoxide ($KO^tBu$), metal amides such as lithium bis(trimethylsilyl)amide (LiHMDS), metal hydrides such as NaH, amidines such as 1,8-diazabicyclo[5.4.0]undec-7-ene (DBU), and phosphazene bases. In preferred embodiments, the base is $KO^tBu$. SN-38 in an appropriate solvent is first contacted with the base at a temperature between −20 and 25° C., preferably between −20 and 5° C., and most preferably at 4° C., so as to produce the phenolate salt. The phenolate is then contacted with N-(chloromethyl)-carbamate (VI) at a temperature between −20 and 25° C., preferably between −20 and 5° C., and most preferably at 4° C., so as to produce a solution of the azido-linker-SN-38 (VII). Appropriate solvents include THF, DMF, and mixtures thereof.

Figure 3:
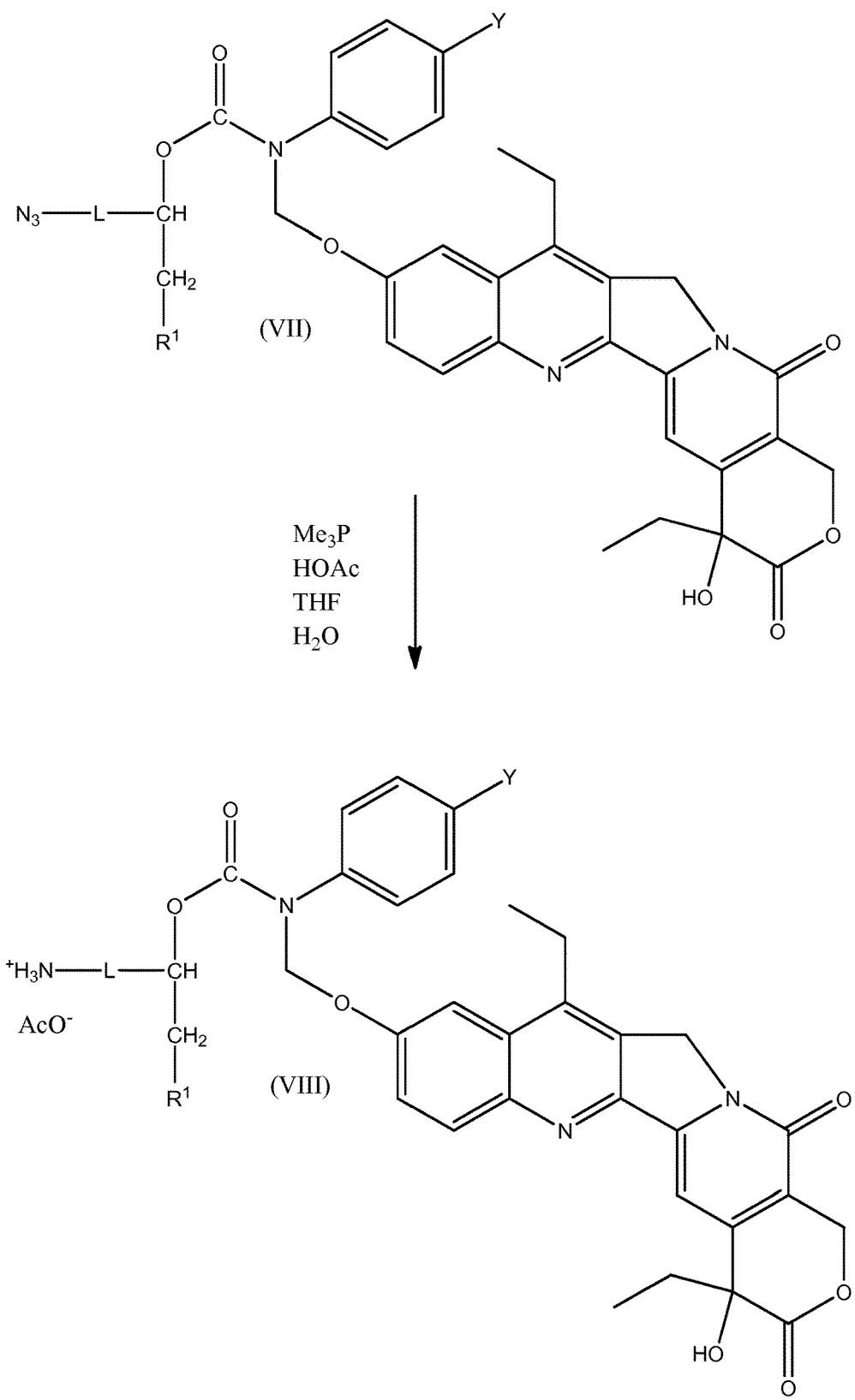
FIG. 3 illustrates one method for the reduction of azido-linker-SN-38 (VII) to amine-linker-SN-38 (VIII) using trimethylphosphine and acetic acid in THF/water.

As illustrated in FIG. 3, the azido-linker-SN-38 (VII) is converted into the amino-linker-SN-38 (VIII) by reduction of the azide. This reduction may be accomplished by a number of means, including catalytic hydrogenolysis in the presence of a metal catalyst such as palladium or platinum; Staudinger reduction using a phosphine such as a trialkylphosphine or triarylphosphine; or indium reduction in the presence of a silane. When significantly basic trialkylphosphines such as trimethylphosphine are used, sufficient acid is added to moderate the basicity of the reaction and thus prevent premature cleavage of the beta-elimination linker. In a preferred embodiment, trimethylphosphine-acetic acid in THF/water is used to convert (VII) to (VIII).

Figure 4:
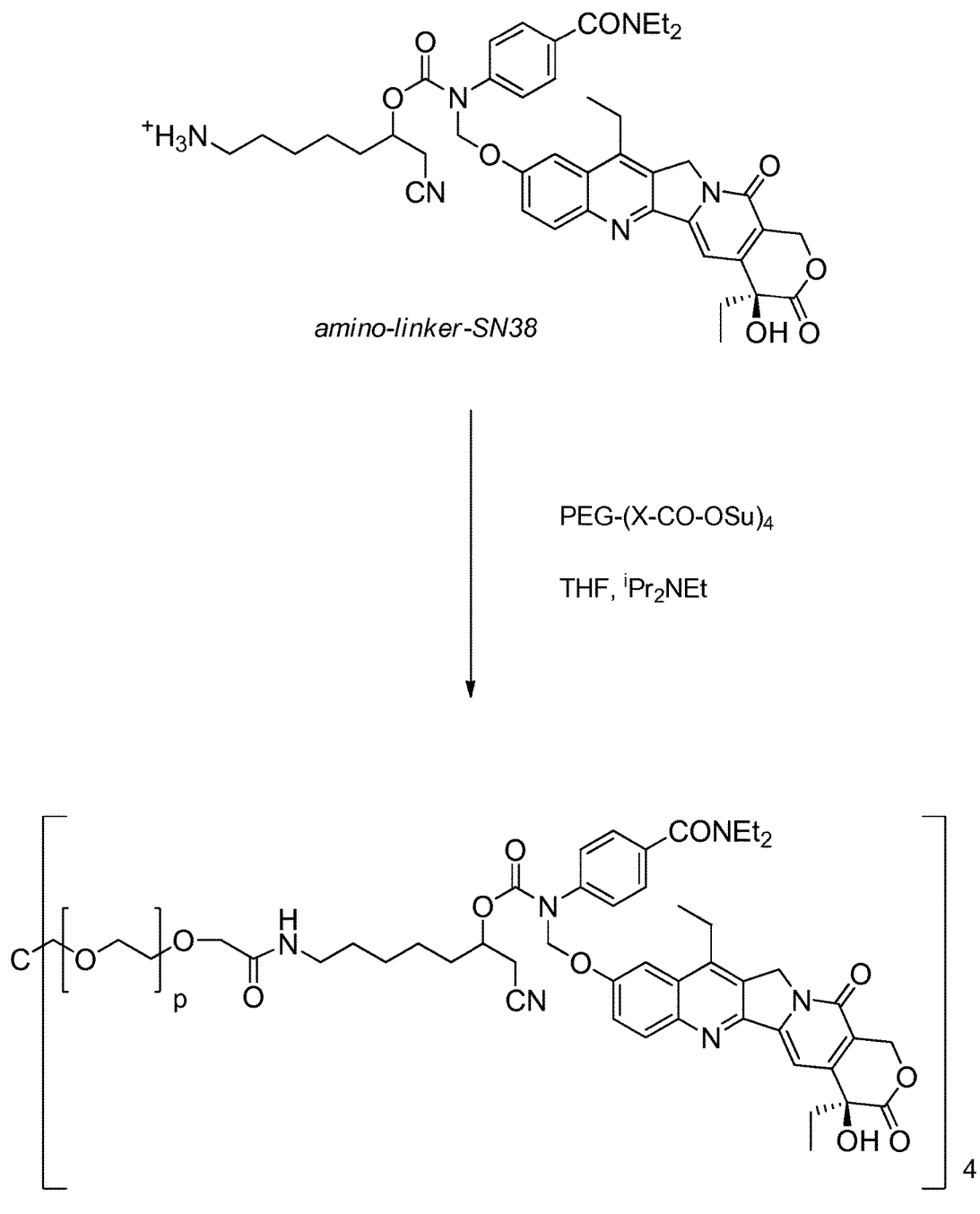
FIG. 4 illustrates one method for the preparation of conjugates (I) of the invention, wherein $R^1$ is CN, Y is $CONEt_2$, q=4, X is $CH_2$, L is $(CH_2)_5$, and PEG is a 4-arm poly(ethylene glycol) having a pentaerythritol core.
Figure 5:
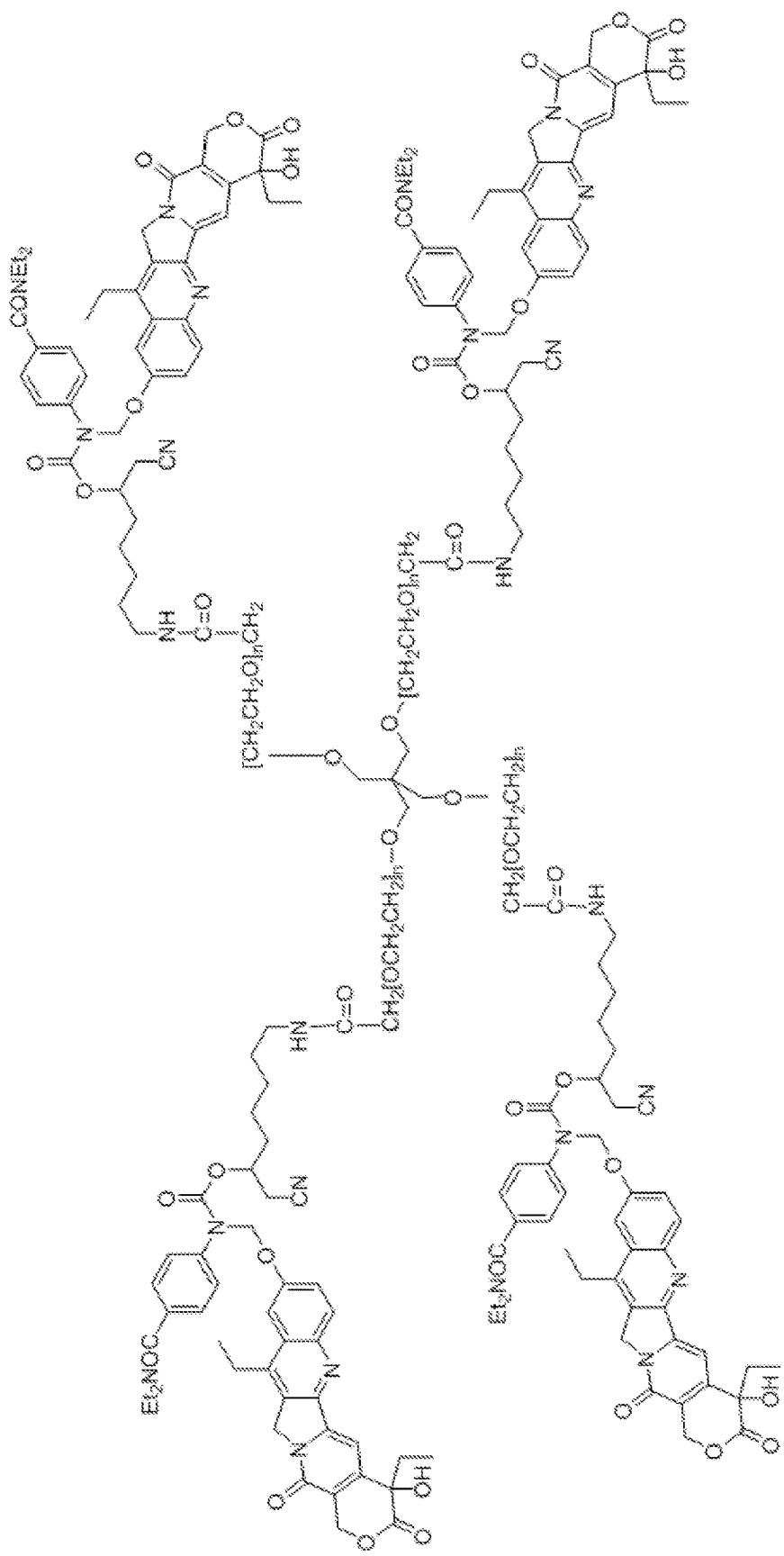
FIG. 5 shows the detailed structure of one conjugate of formula (I) wherein $R^1$ is CN, Y is $CONEt_2$, q=4, X is $CH_2$, L is $(CH_2)_5$, and PEG is a 4-arm poly(ethylene glycol) of average molecular weight 40,000 (n~225).

The amine-linker-SN-38 (VIII) is connected to an activated PEG to provide the conjugate (I) as illustrated in FIG. 4. Suitably activated PEGs have polymer chains terminated with an amine-reactive functional group, such as an N-hydroxysuccinimide (NHS) ester, a pentahalophenyl ester, or a nitrophenyl ester to produce conjugates of formula (I) wherein X is absent, and an N-hydroxysuccinimidyl carbonate, pentahalophenyl carbonate, or nitrophenyl carbonate to produce conjugates of formula (I) wherein X is O. Alternatively, a PEG wherein the polymer chains are terminated with a carboxylic acid may be used in the presence of a peptide coupling agent such as a carbodiimide like DCC or EDCI or a phosphonium reagent like BOP or PyBOP, or uronium reagent like HATU or HBTU. Coupling is performed in aqueous or anhydrous conditions, preferably anhydrous in a suitable solvent such as acetonitrile, THF, DMF, or dichloromethane. In a preferred embodiment, an activated PEG having the polymer chains terminated with an NHS ester is used in THF solvent at temperatures between 0 and 25° C.

The resulting conjugates may be purified using methods known in the art. For example, the conjugate may be precipitated from the reaction mixture by addition of an ethereal solvent such as ethyl ether or methyl tert-butyl ether (MTBE). The conjugate may also be purified by dialysis or by size-exclusion chromatography.

In a third aspect, the invention provides methods for the slow release of SN-38 using conjugates of formula (I). In one embodiment, the half-life for release of SN-38 from the conjugate is between 100 and 1000 hours, preferably between 300 and 500 hours, and more preferably approximately 400 hours.

In another embodiment of the invention, a method of providing continuous, low-dose exposure to SN-38 to a patient in need of such exposure comprising administering to the patient a conjugate of the invention is provided. In a more specific embodiment, a method wherein the concentration of free SN-38 is maintained between 15 and 5 nM between once-weekly administrations is provided.

In another embodiment of the invention, a method for controlling the $C_{max}/C_{min}$ ratio of SN-38 observed between administrations of a conjugate is provided. The resulting $C_{max}/C_{min}$ ratio is less than or equal to 10 between once-weekly administrations, more preferably less than or equal to 5, and more preferably approximately 2.5.

Figure 6:
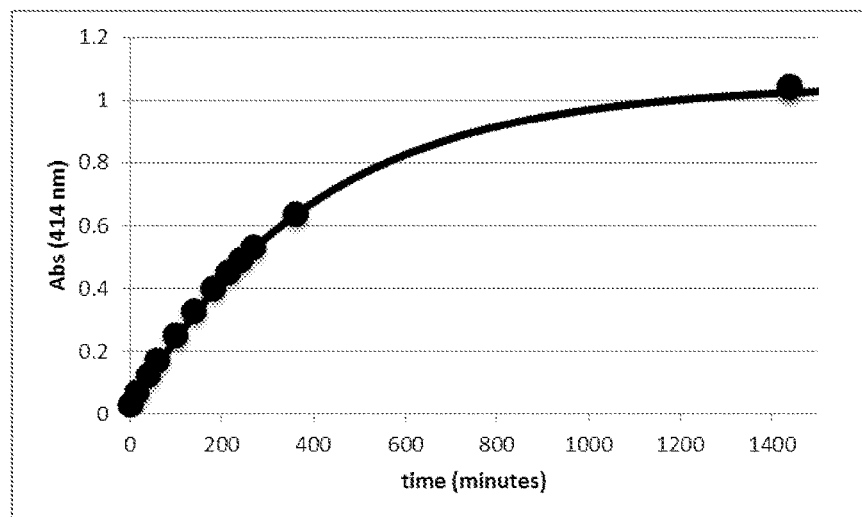
FIG. 6 shows in vitro release kinetics of SN-38 from the conjugate of the invention wherein $R^1$ is CN, Y is $CONEt_2$, q=4, X is $CH_2$, L is $(CH_2)_5$, and PEG is a 4-arm poly(ethylene glycol) of average molecular weight 40,000. SN-38 has a $pK_a$~8.6 due to ionization of the 10-OH; upon formation of the phenolate, the UV/Vis absorbance maximum of SN-38 shifts to 414 nm. When conjugated through the 10-OH, SN-38 shows no absorbance at 414 nm. Thus, the increase in absorbance at 414 nm is a measure of the formation of free SN-38 from the conjugate. The curve indicated was fit to the experimental data using a first-order rate constant of 0.00257 min$^{-1}$ at pH 9.4. This translates to a $t_{1/2}$ for release of 450 hours at pH 7.4.

As shown in FIG. 6, the conjugate of formula (II) wherein PEG is a 4-armed polyethylene glycol (pentaerythritol core) of average molecular weight 40,000 [i.e., formula (I) wherein q=4; X is $CH_2$; $R^1$ is CN; Y=$CONEt_2$, PEG is a 4-armed poly(ethylene glycol) of average molecular weight 40,000; and L is $(CH_2)_5$] when placed in pH 9.4 buffer at 37° C. released free SN-38 in a first-order process having a half-life of 4.5 hours. It has been demonstrated that the beta-elimination linkers used herein show a first-order release rate dependence on pH, such that the corresponding half-life for release at physiological pH (7.4) can be calculated to be 450 hours.

Figure 7:
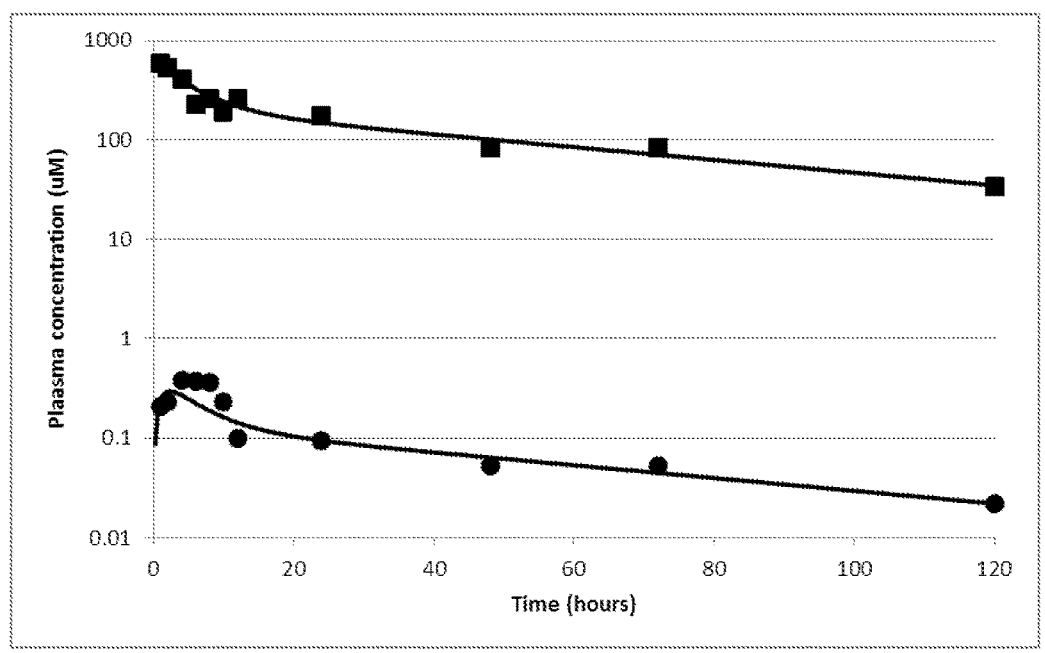
FIG. 7 shows in vivo levels of conjugate (squares) and free SN-38 (circles) released from the conjugate of formula (I) wherein $R^1$ is CN, Y is $CON(Et)_2$, q=4, X is $CH_2$, L is $(CH_2)_5$, and PEG is a 4-arm poly(ethylene glycol) of average molecular weight 40,000, after i.v. administration of 200 mg/kg of conjugate (7 mg/kg of SN-38) to rats (average of n=3). The curves were generated as described in Example 5 using an in vivo release $t_{1/2}$=400 h.
Figure 8:
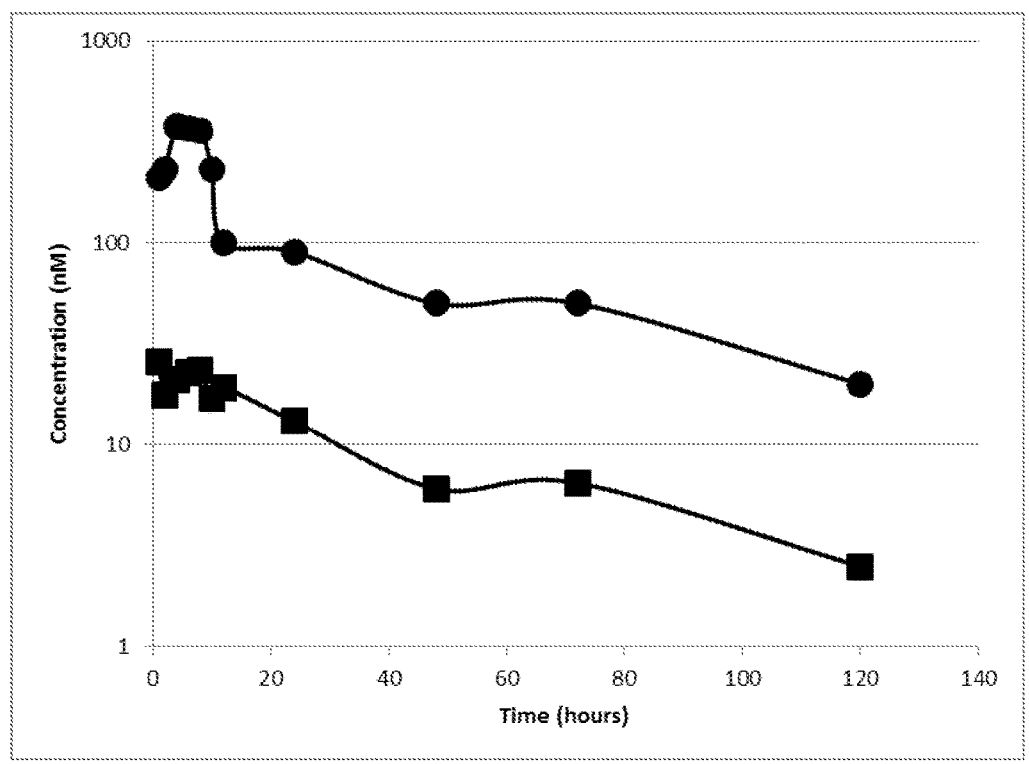
FIG. 8 shows in vivo levels of free SN-38 (circles) and SN-38 glucuronide (squares) formed from the conjugate of formula (I) wherein $R^1$ is CN, Y is $CON(Et)_2$, q=4, X is $CH_2$, L is $(CH_2)_5$, and PEG is a 4-arm poly(ethylene glycol) of average molecular weight 40,000, after i.v. administration of 200 mg/kg of conjugate (7 mg/kg of SN-38) to rats (average of n=3).

As shown in FIG. 7, when the same conjugate was administered to rats by i.v. injection free SN-38 was released and followed a concentration versus time profile parallel to that of the conjugate with a terminal half-life of approximately 51 h. This compares with direct i.v. administration of SN-38, which shows a terminal half-life of between 7 and 34 minutes in rats (Atsumi, et al., "Pharmacokinetics of SN-38 [(+)-(4S)-4,11-diethyl-4,9-dihydroxy-1H-pyrano[3',4':6,7]- indolizino[1,2-b]quinoline-3,14(4H,12H)-dione], an active metabolite of irinotecan, after a single intravenous dosing of 14C—SN-38 to rats," *Biol. Pharm. Bull.* (1995) 18:1114-1119; Kato, et al., "Panipenem Does Not Alter the Pharmacokinetics of the Active Metabolite of Irinotecan SN-38 and Inactive Metabolite SN-38 Glucuronide (SN-38G) in Rats," *Anticancer Res.* (2011) 31:2915-2922). Thus, the conjugates of the invention significantly extend the in vivo half-life of SN-38.

The levels and observed terminal half-life of a drug released from a conjugate are the result of the combination of the pharmacokinetic parameters of the conjugate and drug, with the terminal half-life being the sum of the conjugate elimination and drug release rates in a simple one-compartment model (Santi, et al., "Predictable and Tunable Half-life Extension of Therapeutic Agents by Controlled Chemical Release from Macromolecular Conjugates," *Proc. Natl. Acad. Sci. USA* (2012) 109:6211-6216). In order to determine these parameters, the data were analyzed using a pharmacokinetic model wherein the conjugate is distributed between two compartments and can release free SN-38 before being cleared. To establish the clearance rate of the conjugate itself ($k_{el}$), the analogous stable conjugate (formula (II) wherein $CH_2CN$ is absent) was administered i.v. to rats and the pharmacokinetic parameters were obtained using a two-compartment model.

As shown in FIG. 7, the concentration versus time data are consistent with conjugate (II) releasing free SN-38 in vivo with a half-life of approximately 400 h. After a single injection of conjugate (II) in rats at 200 mg/kg (comprising 7 mg/kg of SN-38), plasma levels of SN-38 were observed to span 210-20 nM over 7 days (i.e., $C_{max}/C_{min}=10$). The terminal half-life of the conjugate and correspondingly the free SN-38 is limited by the relatively fast elimination rate of the conjugate in the rat. The elimination rate of a PEG conjugate is species-dependent due to differential rates of renal filtration, with the terminal half-life of a 40,000-Da PEG being approximately 12 h in mouse, 24-48 h in rats, and 72-120 h in humans. Further, it is typically the case that the elimination rates of drugs are slower in human patients than in rats (see, for example, Caldwell, et al., "Allometric scaling of pharmacokinetic parameters in drug discovery: can human CL, Vss and t1/2 be predicted from in-vivo rat data?," *Eur J Drug Metab Pharmacokinet.* (2004) 29:133-143). Thus, the terminal half-life of SN-38 released from a conjugate of formula (I) is expected to be substantially longer in humans than in rodents, even though the rate of drug release from the conjugate is expected to be relatively species-independent due to the consistency of blood pH values. While the actual pharmacokinetic parameters for conjugates of the invention and of free SN-38 in human patients are unknown, estimation of these values using allometric scaling provides an estimate of $C_{max}/C_{min}\sim2.5$ in human patients as described below in Example 5. Prolonged infusion of the SN-38 prodrug irinotecan in human patients has indicated that maximum efficacy may be obtained if the plasma levels of SN-38 are maintained between about 5 and 15 nM for prolonged periods. The rat pharmacokinetic data thus predicts that the conjugates of the invention enable the release of continuous low, efficacious levels of SN-38.

Surprisingly, the levels of SN-38G observed upon treating rats with the conjugate of formula (II) were extremely low, with SN-36G/SN-38≤0.1 at $C_{max}$. This contrasts with treatment with ester-linked irinotecan conjugates (SN-38G/SN-38~15 at $C_{max}$; Eldon, et al., "Population Pharmacokinetics of NKTR-102, a Topoisomerase Inhibitor-Polymer Conjugate in Patients With Advanced Solid Tumors," American Society of Clinical Oncology Poster 8E (2011)), or with ester-linked SN-38 conjugates (SN-38G/SN-38~1 at $C_{max}$; Patnaik, et al., "EZN-2208, a novel anticancer agent, in patients with advanced malignancies: a Phase 1 dose-escalation study," *American Association for Cancer Research Poster C221* (2009)). It thus appears that SN-38 is less effectively glucuronidated when very slowly released. In accord with this hypothesis, when a conjugate having $R^1=PhSO_2$ was examined in rats, faster release of SN-38 ($t_{1/2}=10$ h) was observed as expected, concomitant with higher initial levels of free SN-38 and a higher SN-38G/SN-38=0.2 at $C_{max}$.

Thus, in a fourth aspect, the invention provides methods for minimizing the amount of SN-38 glucuronide formed upon administration of SN-38 by control of the release rate of SN-38 from a conjugate. In one embodiment of the invention, a method for minimizing the amount of SN-38 glucuronide formed upon administration of SN-38 is provided wherein a conjugate characterized by a half-life for SN-38 release of greater than 100 hours is provided. In a more specific embodiment, the half-life for SN-38 release is between 100 and 1000 hours. In a preferred embodiment, the half-life for SN-38 release is between 300 and 500 hours. In an even more preferred embodiment, the half-life for SN-38 release is approximately 400 hours.

The conjugates of the invention may be formulated using a variety of pharmaceutically acceptable excipients known in the art, and are conveniently formulated in aqueous buffer having a pH optimal for conjugate stability. In one embodiment of the invention, the conjugates are formulated in aqueous buffer at a pH value between 4 and 6. It has been unexpectedly found that the conjugates of formula (I) are significantly more soluble in aqueous buffer than the related conjugates disclosed in WO2011/140393 (see Example 2 below), thus enabling a greater range of dosing to patients in need of therapy with these compounds.

The conjugates of the invention are expected to find utility in any situation where SN-38 or a prodrug of SN-38, for example irinotecan, have utility. At present, irinotecan is used in the treatment of various cancers, including leukemia, lymphoma, colorectal, lung, ovarian, cervical, pancreatic, stomach, and breast cancers, and it is thus anticipated that the conjugates of the invention may be used similarly.

In an alternative embodiment illustrated in Example 6 a formulation of SN-38 provides a solubilized form when the excipients include PEG and DMSO. This is particularly useful for continuous infusion, for example. The ratio of PEG to DMSO varies from 90:10-10:90, but also may be 75:25, 25:75 or 50:50 or intermediate values thereof. The useful PEG components range from approximately PEG100 (100)-PEG(600).

Unless otherwise indicated, all references are hereby incorporated by reference in their entirety.

EXAMPLES

General:HPLC was performed using a Shimadzu HPLC system with diode-array detection. Reversed-phase used a Phenomenex® Jupiter 5 um 300 A 4.6×150 mm column thermostatted at 40° C., with a 20-100% gradient of acetonitrile in water containing 0.1% TFA at a flow rate of 1.0 mL/min. Size-exclusion HPLC used a Phenomenex® Bio-Sep™ S-2000 column running 50:50 acetonitrile/water/0.1% TFA at 40° C. Solutions containing SN-38 were quantitated by UV absorbance at 363 nm in acetonitrile using e=22,500 $M^{-1}cm^{-1}$. SN-38 was purchased from Haorui (China).

Preparation A 6-azido-1-hexanol

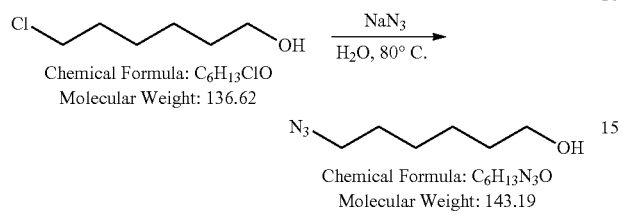

A mixture of 6-chloro-1-hexanol (50.0 g, 366 mmol) and sodium azide (65.0 g, 1000 mmol) in 400 mL of water was heated at a gentle reflux for 19 h. After cooling to ambient temperature, the mixture was extracted 3×200 mL of EtOAc. The extract was washed 1×100 mL of water, 1×100 mL of sat. aq. NaCl, then dried over $MgSO_4$, filtered, and evaporated to yield 44.9 g (86%) of a colorless oil. $^1$H-NMR (400 MHz, $CDCl_3$): δ 3.66 (2H, br t, J=6 Hz), 3.27 (2H, t, J=7.2 Hz), 1.55-1.66 (m, 4H), 1.38-1.44 (m, 2H).

Preparation B 6-azidohexanal

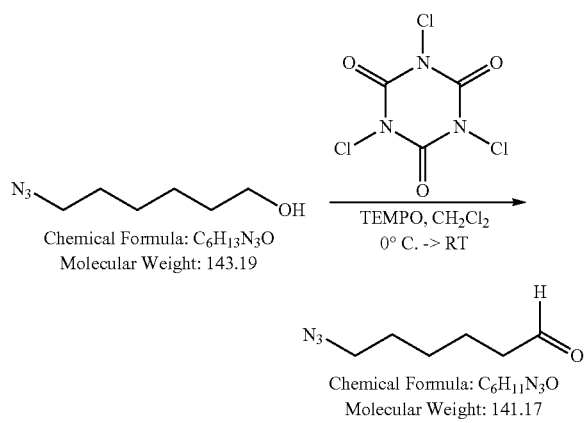

Trichloroisocyanuric acid (12.2 g, 52.5 mmol) was added to a vigorously-stirred solution of 6-azido-1-hexanol (7.2 g, 50.0 mmol) in 100 mL of dichloromethane cooled on ice. A solution of TEMPO (0.080 g, 0.51 mmol) in 2 mL of dichloromethane was added dropwise to the resulting suspension. After 10 min at 4° C., the suspension was allowed to warm to ambient temperature and stirred for an additional 30 min. TLC analysis (30% EtOAc/hexane) indicated complete reaction. The suspension was filtered through a 1 cm pad of Celite using dichloromethane. The filtrate was washed 2×100 mL of 1 M $Na_2CO_3$, 1×100 mL of water, 1×100 mL of 1 N HCl, and 1×100 mL of sat. aq. NaCl, then dried over $MgSO_4$, filtered, and evaporated to yield 9.8 g of an orangish oil. This was dissolved in a small volume of dichloromethane and chromatographed on $SiO_2$ (80 g) using a gradient of 0-20% EtOAc/hexanes to provide 6.67 g (47.3 mmol; 95%) of the aldehyde as a colorless oil. $^1$H-NMR (400 MHz, $CDCl_3$): δ 9.78 (1H, t, J=1.6 Hz), 3.29 (2H, t, J=6.8 Hz), 2.47 (2H, dt, J=1.6, 7.6 Hz), 1.59-1.71 (m, 4H), 1.38-1.46 (m, 2H).

Preparation C 7-azido-1-cyano-2-heptanol

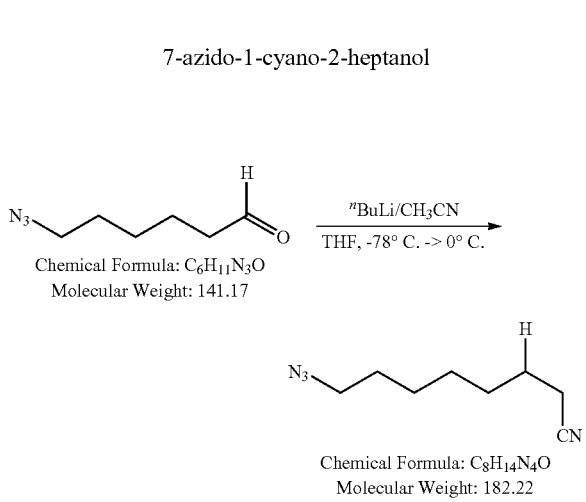

A 1.6 M solution of n-butyllithium in hexane (35 mL, 49 mmol) was added to 100 mL of anhydrous THF under $N_2$ at −78° C. Acetonitrile (3.14 mL, 60 mmol) was added in a rapid stream with vigorous stirring, resulting in formation of a white suspension. After 15 min, the suspension was allowed to warm to −20° C. for over 1 h. After cooling back to −78° C., 6-azidohexanal (6.67 g, 47 mmol) was added resulting in a yellow solution. This was stirred for an additional 15 min, then allowed to warm to −20° C. and quenched by addition of 20 mL of sat. aq. $NH_4Cl$. After dilution with EtOAc, the mixture was washed sequentially with water, 1 N HCl, water, and sat. aq. NaCl, then dried over $MgSO_4$, filtered, and evaporated to yield 8.0 g of a yellow oil. This was dissolved in a small volume of dichloromethane and chromatographed on $SiO_2$ (80 g) using a gradient of 0-40% EtOAc/hexanes to provide 6.0 g (21.6 mmol; 84%) of the product as a colorless oil. $^1$H-NMR (400 MHz, $d_6$-DMSO): δ 5.18 (1H, d, J=5 Hz), 3.69 (1H, m), 3.32 (2H, t, J=6 Hz), 2.60 (1H, dd, J=4.8, 16.4 Hz), 2.51 (1H, dd, J=6.4, 16.4 Hz), 1.55 (2H, m), 1.42 (2H, m), 1.30 (4H, m).

Preparation D

N,N-diethyl 4-nitrobenzamide

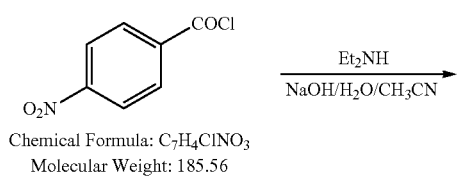

-continued

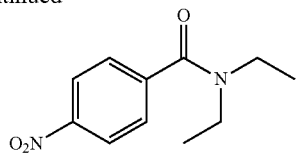

Chemical Formula: C₁₁H₁₄N₂O₃
Molecular Weight: 222.24

A solution of 4-nitrobenzoyl chloride (18.6 g, 100 mmol) in 100 mL of acetonitrile was added dropwise over 30 min to a stirred ice-cold solution of diethylamine (15.5 mL, 150 mmol) and sodium hydroxide (6.0 g, 150 mmol) in 150 mL of water. After completion of addition, the mixture was allowed to warm to ambient temperature and stirred for an additional 1 h. The mixture was extracted 3×100 mL of CH₂Cl₂, and the combined extract was washed 1×100 mL of water, 1×100 mL of 1 N HCl, and brine. After drying over MgSO₄, the mixture was filtered and evaporated to dryness to give a crystalline mass. Recrystallization from 80/20 hexane/ethyl acetate provided 20.0 g of product as pale yellow crystals (90%). ¹H-NMR (400 MHz, CDCl₃): δ 8.27 (2H, m), 7.54 (2H, m), 3.57 (2H, br q, J=6.8 Hz), 3.21 2H, br q, J=6.8 Hz), 1.27 (3H, br t, J=6.8 Hz), 1.12 (3H, br t, J=6.8 Hz).

Preparation E 4-(N,N-diethylcarboxamido)aniline

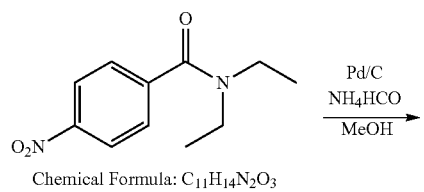

Ammonium formate (20.0 g, 317 mmol) was added to a vigorously stirred mixture of N,N-diethyl 4-nitrobenzamide (20.0 g, 90 mmol) and 1.0 g of 10% palladium/charcoal in 400 mL of methanol cooled on ice. The reaction warms with vigorous gas evolution. After 1 h, TLC (60/40 hexane/EtOAc) indicated complete conversion of the starting material. The mixture was filtered through a pad of Celite and evaporated to a crystalline solid. This was suspended in water and collected by vacuum filtration. The product was recrystallized from water and dried to provide 14.14 g (83%) of white crystals. ¹H-NMR (400 MHz, CDCl₃): δ 7.22 (2H, m), 6.65 (2H, m), 3.81 (2H, br s), 3.42 (4H, br s), 1.17 (6H, t, J=6.8 Hz).

Preparation F 1-cyano-7-azido-2-heptyl 4-(N,N-diethylcarboxamido)phenylcarbamate

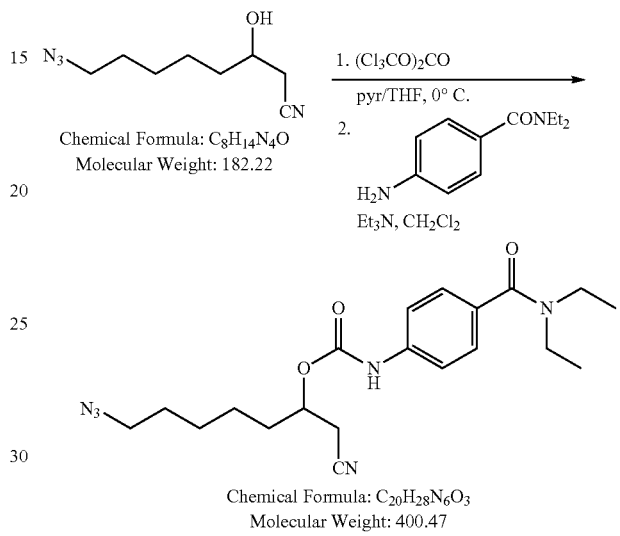

Pyridine (4.0 mL, 50 mmol) was added dropwise under inert atmosphere to a stirred solution of 1-cyano-7-azido-2-heptanol (4.60 g, 25 mmol) and triphosgene (12.5 g, 42 mmol) in 200 mL of anhydrous THF cooled on ice. The white suspension was stirred for 15 min on ice, then allowed to warm to ambient temperature and stirred an additional 30 min. TLC analysis (60:40 hexane/ethyl acetate) indicated complete conversion of starting material to a high-R_f product. The suspension was filtered and evaporated, and the residue was taken up in 100 mL of dry ether, filtered, and evaporated to give the crude chloroformate (4.54 g, 74%) as a brown oil. Triethylamine (3.5 mL, 25 mmol) was added to a solution of the chloroformate (18.6 mmol) and 4-(N,N-diethylcarboxamido)aniline (3.85 g, 20 mmol) in 100 mL of dry CH₂Cl₂. After stirring for 1 hour, the mixture was washed 2× with 1 N HCl, 2× with water, and 1× with brine, then dried over MgSO₄, filtered, and evaporated to an oil that crystallized upon standing. The crystalline mass was washed with 60/40 hexane/ethyl acetate. The washings were concentrated and chromatographed on silica using a gradient of 0-80% ethyl acetate/hexane. The product fractions were concentrated, and combined with the initial crystalline material. The combined product was recrystallized from 1:1 ethyl acetate/hexane to give the carbamate as a white crystalline solid (4.4 g, 44% for 2 steps). ¹H-NMR (CDCl₃, 400 MHz): δ 7.45-7.35 (4H, m), 6.888 (1H, br s), 5.000 (1H, m), 3.52 (4H, br), 3.288 (2H, t, J=6.8 Hz), 2.841 (1H, dd, J=5.2, 17 Hz), 2.327 (1H, dd, J=4.4, 17 Hz), 1.88 (1H, m), 1.75 (1H, m), 1.63 (2H, m), 1.45 (4H, m), 1.18 (6H, br).

Preparation G

N-(chloromethyl)carbamate

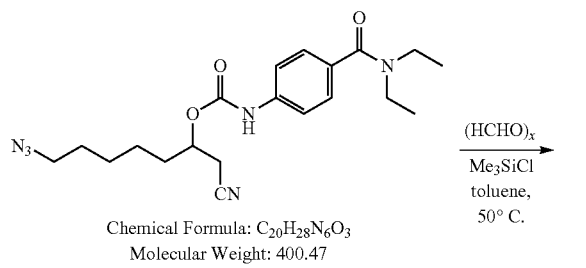

Chemical Formula: C$_{20}$H$_{28}$N$_6$O$_3$
Molecular Weight: 400.47

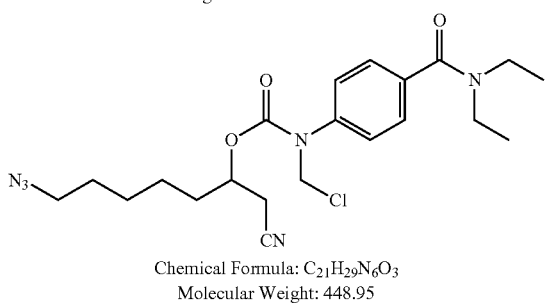

Chemical Formula: C$_{21}$H$_{29}$N$_6$O$_3$
Molecular Weight: 448.95

A suspension of 7-azido-1-cyano-2-hexyl N-(chloromethyl)-4-(N,N-diethylcarboxamido)-phenylcarbamate (2.00 g, 5.0 mmol), paraformaldehyde (225 mg, 5.5 mmol, 1.5 Eq), chlorotrimethylsilane (2.5 mL, 20.0 mmol, 4.0 Eq), and 25 mL of anhydrous toluene was placed under N$_2$ atmosphere in a 50-mL RBF fitted with a magnetic stir bar and closed with a rubber septum cap. The sealed flask was heated in a 50° C. oil bath for 24 h, at which time a clear yellow solution was obtained. The solution was cooled to ambient temperature and evaporated. The residue was redissolved in 10 mL of dry toluene, filtered, and evaporated to provide the crude N-(chloromethyl)-carbamate as an unstable yellow oil containing residual toluene (2.68 g, 119% of expected). This material was dissolved in 10 mL of anhydrous THF and stored under N$_2$. Formation of the N-(chloromethyl)carbamate was confirmed by addition of 5 uL to 1.0 mL of 4 mM N,N-diisopropylethylamine in ethanol, followed by reversed-phase HPLC analysis (Phenomenex Jupiter 300A 4.6×150 mm C$_{18}$; 1.0 mL/min; gradient from 20-100% CH$_3$CN/H$_2$O/0.1% TFA over 10 min). Starting carbamate elutes at 8.42 min and shows λ$_{max}$ 243 nm; product N-(ethoxymethyl)-carbamate elutes at 8.52 min and shows λ$_{max}$ 231 nm; an unknown impurity elutes at 8.04 min and shows λ$_{max}$ 245 nm. Peak integration at 240 nm indicated approximately 89% N-(ethoxymethyl)-carbamate. $^1$H-NMR (400 MHz, CDCl$_3$): δ 7.39 (4H, m), 5.54 (1H, d, J=12 Hz), 5.48 (1H, d, J=12 Hz), 4.99 (1H, m), 3.51 (4H, br), 3.26 (2H, t, J=6.8 Hz), 2.79 (1H, m), 2.63 (1H, m), 1.85 (1H, m), 1.73 (1H, m), 1.60 (2H, m), 1.43 (4H, m), 1.16 (6H, br).

Preparation H

Azido-linker-SN-38

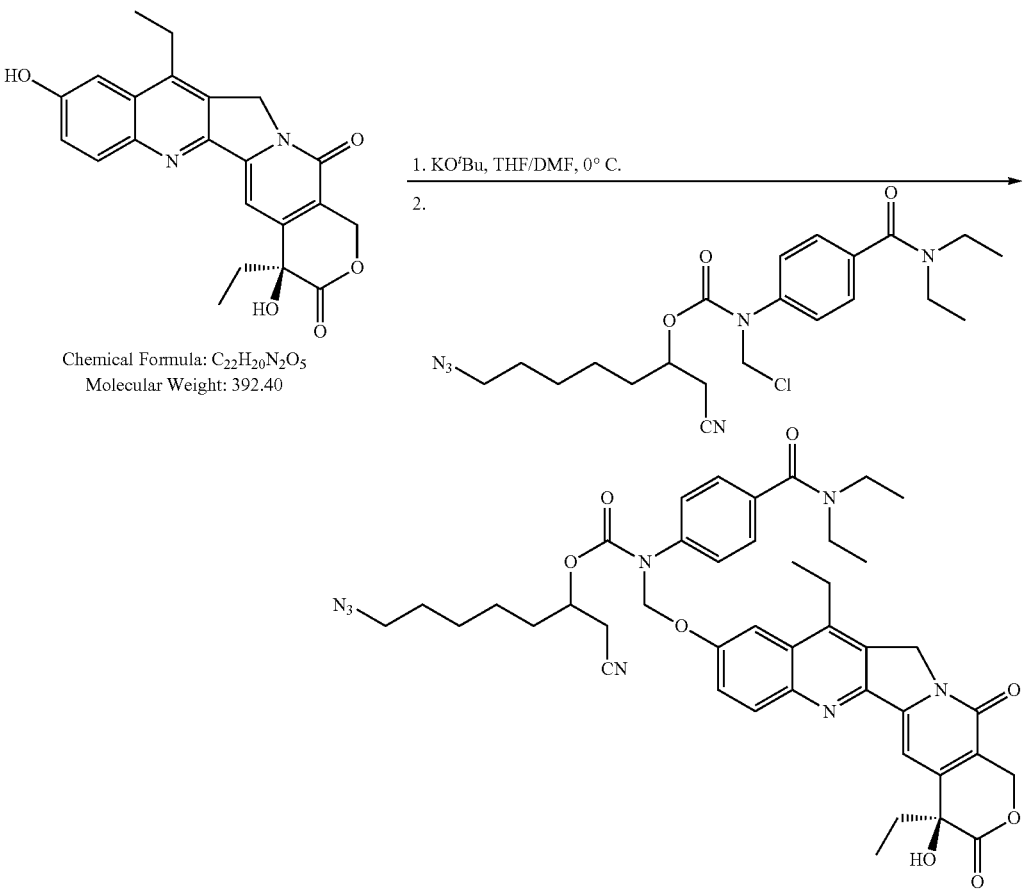

Chemical Formula: C$_{43}$H$_{48}$N$_8$O$_8$
Molecular Weight: 804.89

SN-38 (1.00 g, 2.55 mmol; Haorui) was suspended in 10 mL of anhydrous pyridine, and then concentrated to dryness under vacuum (bath temperature 50° C.). This was repeated with 10 mL of anhydrous THF. The resulting pale yellow solid was dissolved in 50 mL of anhydrous THF and 50 mL of anhydrous DMF under $N_2$ atmosphere, and then cooled on ice. A 1.0 M solution of potassium tert-butoxide in THF (2.55 mL, 2.55 mmol) was added forming an initial dark green color that changed to a thick orange suspension. After 15 min, a THF solution of the N-(chloromethyl)-carbamate (7.5 mL, 2.8 mmol) was added. After 15 min at 4° C., the light orange mix was allowed to warm to ambient temperature. After 1 hr, HPLC analysis (5 uL of sample+1 mL of acetonitrile/0.1% TFA) indicated 86/14 product/SN-38. The pale yellow mixture was diluted with 200 mL of ethyl acetate, washed 2×100 mL of water, 100 mL of sat. aq. NaCl, dried over $MgSO_4$, filtered, and evaporated. Excess DMF was removed by trituration of the oily residue with water, and the residue was dissolved in 50 mL of acetonitrile, filtered, and evaporated to yield 2.96 g of yellow glass. The residue was chromatographed on $SiO_2$ (80 g) using a step gradient of 200 mL each of hexane, 20%, 40%, 60%, 80%, and 100% acetone in hexane, providing the purified azido-linker-SN-38 (1.66 g, 81%). This material was dissolved in 50 mL of acetone, and 45 mL of 0.1% acetic acid in water was added dropwise with stirring until the mixture became cloudy. Upon stirring, a solid material separated. An additional 5 mL of 0.1% acetic acid in water was then added to complete the precipitation. After stirring for 2 h, the solid was collected by vacuum filtration, washed with water, and dried to provide 1.44 g (70%) of pale yellow powder. $^1$H-NMR (400 MHz, $CDCl_3$): δ 8.15 (1H, d, J=9.2 Hz), 7.60 (1H, s), 7.48 (1H, dd, J=2.9 Hz), 7.40 (4H, m), 7.25 (1H, d, J=2), 5.75 (2H, br), 5.73 (1H, d, J=16 Hz), 5.28 (1H, d, J=16 Hz), 5.22 (2H, s), 4.99 (1H, m), 3.84 (1H, s), 3.53 (2H, br), 3.53 (2H, br), 3.17 (2H, t, J=7 Hz), 3.12 (2H, q, J=7 Hz), 2.74 (1H, dd, J=1, 17 Hz), 2.54 (1H, dd, J=5, 17), 1.86 (2H, m), 1.6 (1H, m), 1.46 (1H, m), 1.37 (3H, t, J=7 Hz), 1.25 (6H, m), 1.12 (4H, m), 1.02 (3H, t, J=7.3 Hz). LC-MS: $[M+H]^+$=805.3 (calc. for $C_{44}H_{51}N_8O_8$=805.3).

Example 1

Amino-linker-SN-38 acetate salt

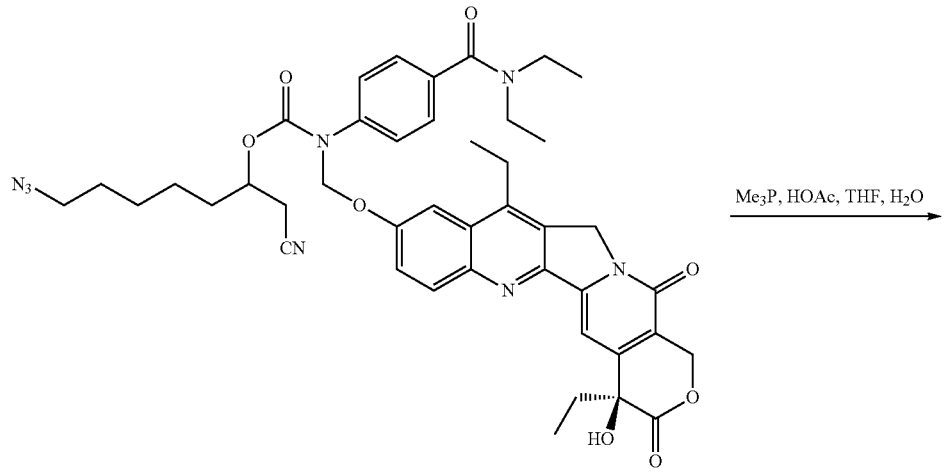

Chemical Formula: $C_{43}H_{48}N_8O_8$
Molecular Weight: 804.89

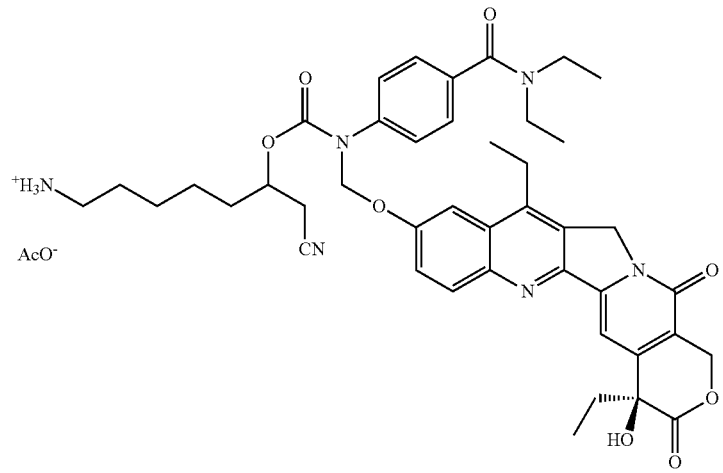

Chemical Formula: $C_{45}H_{54}N_6O_{10}$
Molecular Weight: 838.94

A 1 M solution of trimethylphosphine in THF (2.9 mL, 2.9 mmol) was added to a solution of the azido-linker-SN-38 (1.13 g, 1.4 mmol) and acetic acid (0.19 mL, 3.3 mmol) in 10 mL of THF. Gas was slowly evolved. After stirring for 2 h, water (1.0 mL) was added and the mixture was stirred for an additional 1 h. The residue was partitioned between ether and water. The water phase was washed once with ethyl acetate, and the resulting clear yellow aqueous phase was evaporated to provide 800 mg of yellow foam. This was dissolved in THF, filtered, and quantitated by UV absorbance to provide a solution containing 1.2 μmol (86%) of product. $C_{18}$ HPLC showed a single peak, and LC-MS showed $[M+H]^+$=779.3 (expected 779.4).

Example 2

SN-38 Conjugate with Compound (III) wherein m=1 and n~225

A mixture of 40 kDa 4-arm tetra-(succinimidyl-carboxymethyl)-PEG (JenKem Technology; 10.0 g, 1.0 mmol HSE), the amino-linker-SN-38 acetate salt of Example 1 (1.2 mmol), and N,N-diisopropylethylamine (0.21 mL, 1.2 mmol) in 75 mL of THF was kept at ambient temperature. Coupling progress was monitored by HPLC, which indicated completion of reaction by 90 minutes. After a total of 2 h, the mixture was filtered into 500 mL of stirred MTBE. The precipitate was collected by vacuum filtration, washed with MTBE, and dried under vacuum to provide the conjugate as a waxy pale yellow solid (10.1 g, 95%). Spectrophotometric analysis of a 2.0 mg sample in 1.0 mL of water indicated 0.17 mM SN-38; based on the calculated 0.175 mM SN-38 expected by weight, this indicates a conjugate loading of 96%. $C_{18}$-HPLC analysis indicated a single major peak (98% of total peak area at 363 nm; 97% at 256 nm), with 0.6 mol % of free SN-38.

This conjugate was soluble to 1.9 mM (85 mg/mL) in 10 mM sodium acetate buffer, pH 5.0. In contrast, the corresponding conjugate wherein the azido-linker-SN-38 of Preparation H had been connected to $PEG_{40\,kD}$-$(DBCO)_4$ via a triazole linkage (WO2011/140393) was soluble to only 0.7 mM (32 mg/mL). Solubility of the example 2 conjugate was also tested at pH 4 and pH 5 in 0.2 N acetate buffer and at pH 6, pH 7 and pH 8 in 0.2 N phosphate buffer. The solubility was found to be >300 mg/ml at all these pH's. The pH, however, was altered slightly when the conjugate was dissolved and generally increased over the original value. Thus, when 300 mg/ml of the conjugate was dissolved in pH 4 buffer, the pH became 4.5; in pH 5 buffer, the pH became 5.4; in pH 6 buffer, the pH became 6.2; in pH 7 buffer, the pH became 7.2 and in pH 8 buffer, the pH became 7.7.

Stability was also tested when 10 mg/ml of the conjugate was dissolved at room temperature at buffers from pH 47-pH 8 and in water and kept at room temperature for seven days. The purity of the conjugate in the various buffers was determined by HPLC.

Typically, the purity on Day 0 was measured at slightly less than 100%, typically around 97%. There was little if any change in measured purity over seven days at any tested pH in water.

Example 3

In Vitro Release Kinetics

A solution of the conjugate of Example 2 in 0.1 M sodium borate, pH 9.4, was kept in a sealed UV cuvette at 37° C. The increase in absorbance at 414 nm due to formation of free SN-38 phenoxide was monitored with time. Fitting of the data to a single exponential $A_{max}*(1-e^{-kt})$ provided the rate constant for release of SN-38, k, from the conjugate at pH 9.4, where $A_{max}$ is the absorbance at complete reaction. As shown in FIG. 6, formation of free SN-38 followed first-order kinetics with k=0.00257 $min^{-1}$ ($t_{1/2}$=270 min) at pH 9.4. As the rate of release of these linkers is known to be first-order in hydroxide, the release rate at other pH values can be calculated as $k(pH)=k_{9.4}*10^{(pH-9.4)}$. Thus, the rate of SN-38 at pH 7.4 is calculated to be $2.57\times10^{-5}$ $min^d$, or $t_{1/2}$=450 h at pH 7.4, 37° C.

Example 4

In Vivo Pharmacokinetics

A 45 mg/mL solution of the conjugate of Example 2 in 10 mM sodium acetate buffer, pH 5.0, was sterile filtered and injected into cannulated female Sprague-Dawley rats (n=3) at 200 mg/kg, and blood samples (0.3 mL) were drawn periodically and immediately added to 30 μL of a 1 M citrate/0.1% Pluronic® F68 solution, pH 4.5 to lower the sample pH, coagulate, and stabilize the remaining intact conjugate. The samples were centrifuged at approximately 1,500×g (force) for 10 minutes at 2 to 8° C. to remove red blood cells and obtain~150 uL plasma. The plasma was divided into 2 aliquots and transferred to cryogenic vials and stored in a freezer at −80° C. prior to analysis.

For analysis, the samples were thawed on ice and mixed with 2 volumes of acetonitrile/0.5% acetic acid containing 8 ng/mL of camptothecin as internal standard. Precipitated protein was removed by centrifugation at 16,000×g for 10 min at 4° C. Sample supernatants (20 uL) were analyzed using a Phenomenex® 300 Å Jupiter 5 um 150×4.6 mm C18 HPLC column thermostatted at 40° C. using a gradient of 100 mM sodium phosphate, 3 mM heptane sulfonate, pH 4.0 (Buffer A) and 75% acetonitrile in water (Buffer B) at 1.0 mL/min. The gradient consisted of 5% B isocratic for 3 min, 20% B isocratic for 3 min, linear gradient from 20-40% B over 5 min, linear gradient from 40-100% B over 2 min, 100% B isocratic for 3 min, 5% B isocratic for 3 min. Sample elution was followed with a diode array detector and a fluorescence detector with excitation set at 370 nm and the emission set at 470 nm for the first 9 min followed by emission at 534 nm for the final 10 min. Concentrations were calculated by comparison of peak areas to standard curves of the conjugate (absorbance 380 nm), and SN-38 (fluorescence Ex: 370 nm; Em: 534 nm). The following retention times were observed: SN-38, 12.7 min; camptothecin, 13.2 min; and conjugate, 14.5 min. Lower limits of quantitation were determined at a peak height of 10 times the signal to noise ratio by fluorescence detection to be SN-38: 0.07 pmoles in 20 μL injection of acetonitrile treated plasma (3.3 nM in acetonitrile treated plasma, 10 nM in original plasma sample). Conjugate: 2.1 pmoles conjugate (8.4 pmoles SN-38) in 20 μL injection acetonitrile treated plasma (100 nM conjugate; 400 nM SN-38) in acetonitrile treated plasma, 300 nM (1200 nM SN-38) in original plasma sample.

To obtain information on the clearance of the intact conjugate from the plasma, a similar experiment was performed using the analogous stable conjugate (formula (II)) wherein $CH_2CN$ is absent) at 22 mg/kg.

Levels of SN-38 glucuronide were determined according to the method of Poujol, et al., "Sensitive HPLC-Fluorescence Method for Irinotecan and Four Major Metabolites in Human Plasma and Saliva: Application to Pharmacokinetic Studies," *Clinical Chemistry* (2003) 49:1900-1908.

Example 5

Pharmacokinetic Modeling

Plasma concentration versus time data for the conjugate were analyzed using a two-phase model where $C(t)=A^*\exp(-\alpha t)+B^*\exp(-\beta t)$ where $A+B=\text{dose}/Vd$. Data were fit using nonlinear regression analysis (Nelder-Mead downhill simplex), then the parameters were deconvoluted according to the established procedures to provide estimates for the rates of transfer between compartments ($k_{12}$ and $k_{21}$) and the rate of conjugate elimination from the central compartment ($k_{el}$). Analysis of the data for the conjugate of Example 2 and the corresponding stable conjugate (wherein $CH_2CN$ is replaced by H) gave the data in Table 1.

TABLE 1

|  | Releasable | Stable |
|---|---|---|
| $C_{max}$ (uM) | 622 | 59 |
| $\alpha\ t_{1/2}$ (h) | 3.8 | 1.2 |
| $\beta\ t_{1/2}$ (h) | 49 | 56 |
| $k_{12}$ (h$^{-1}$) | 0.09 | 0.35 |
| $k_{21}$ (h$^{-1}$) | 0.07 | 0.21 |
| $k_{el}\ t_{1/2}$ (h) | 18 | 20 |
| $V_d$ (L/kg) | 0.10 | 0.12 |

Using these parameters, the free SN-38 concentration data were then fit based on a model wherein the conjugate releases free SN-38 with rate constant $k_1$ and equilibrates with a second compartment with $K_{dist}=V_d/V_c$. Model curves were generated by numerical integration using the following differential equations:

$$\Delta[C_c]=(-k_1[C_c]-k_{12}[C_c]-k_{el}[C_c]+k_{21}[C_p])\Delta t$$

$$\Delta[C_p]=(k_{12}[C_c]-k_{21}[C_p])\Delta t$$

$$\Delta[D_c]=(k_1[C_c]-k_{cf}[D_c])/(1+K_{dist})\Delta t$$

$$K_{dist}=V_d/V_c$$

Where $[C_c]$ and $[C_p]$ are the concentrations of conjugated SN-38 in the central and peripheral compartments, respectively, $[D_c]$ is the concentration of free SN-38 in the central compartment, and the rate constants are as described above; $k_{cf}$ is the rate constant for elimination of free SN-38 from the plasma, and was allowed to vary within the range reported for this parameter (1.4-3.5 h$^{-1}$). Numerical integration was performed over 1000 steps for a time span of 120 h ($\Delta t=0.12$ h) with initial conditions $[C_c]=C_{max}$, $[C_p]=0$, and $[D_c]=0$. The volume of distribution $V_d$ for SN-38 was set at the reported value of 0.18 L/kg, while $V_c$ was set as $V_d$ for the conjugate.

Using this method, the concentration versus time data for conjugated SN-38 and free SN-38 released from the conjugate were fit as shown in FIG. 7. Good agreement with the experimental data was obtained when $k_{cf}=2.77$ h$^{-1}$ ($t_{1/2}=0.25$ h) for elimination of free SN-38 from the plasma, well within the reported range, and when $k_1$ was set at 0.00173 h$^{-1}$, the value measured in vitro ($t_{112}=400$ h for cleavage of SN-38 from the conjugate).

Using this model, the behavior of the conjugate in other species may be predicted given the values for $k_{el}$ and $k_{cf}$ in those species. In human, the values for PEG ($k_{el}$) and SN-38 ($k_{cf}$) elimination as well as the volume of distribution have not been reported but may be estimated using allometric scaling to be approximately $k_{el}=0.0087$ h$^{-1}$ ($t_{1/2}$ 80 h) and $k_{cf}=0.7$ h$^{-1}$ ($t_{1/2}$ 1 h), and $V_{ss}=0.15$ L/kg (Caldwell et al., "Allometric scaling of pharmacokinetic parameters in drug discovery: can human CL, Vss and t1/2 be predicted from in-vivo rat data?," *Eur J Drug Metab Pharmacokinet.* (2004) 29:133-143.) Using these values in the pharmacokinetic model provides estimated concentration ranges of free SN-38 giving $C_{max}/C_{min}\sim 2.5$.

Example 6

Formulation of SN-38 for Continuous Infusion

Therapeutic administration of SN-38 has been limited by the poor aqueous solubility of this drug (7 mg/L in water, 18 uM). A formulation was developed to overcome this limitation. To determine the solubility of SN-38 in various formulations, a 115 mM solution of SN-38 in dimethyl sulfoxide (DMSO) was diluted to give 15, 10, 5, and 2 mM target concentrations in various formulations (Table 2). After standing for 16 h at ambient temperature, precipitated SN-38 was removed by centrifugation at 14,000 rpm for 30 min. The supernatant was diluted 1:200 into 100 mM borate, pH 10.0, and the concentration of SN-38 was determined spectrophotometrically at 414 nm using $\varepsilon_{414}=22,500$ M$^{-1}$cm$^{-1}$. Results are given in Table 2.

TABLE 2

| | Volume Percent Excipients in Formulations | | | | | |
|---|---|---|---|---|---|---|
| | A | B | C | D | E | F |
| PBS, pH 7.4 | 75 | 50 | 35 | 20 | — | — |
| DMSO | 25 | 50 | 50 | 50 | 50 | 10 |
| Ethanol | — | — | 15 | 30 | — | — |
| PEG300 | — | — | — | — | 50 | 90 |
| Solubility (uM) | 210 | 570 | 760 | 2600 | ≥9300 | ≥4600 |

SN-38 in formulations E and F remained completely soluble at the highest concentrations tested. It is expected that polyethylene glycols other than PEG300 may be used to similar advantage. It is further expected that these pharmaceutical formulations may be used to maintain a continuous exposure to SN-38 to a patient in need of such exposure, by administering the pharmaceutical formulation by continuous infusion. Such continuous infusions may be carried out by any of the methods known in the medical arts, for example by use of an infusion pump or by i.v. drip.

What is claimed is:
1. A conjugate having the formula
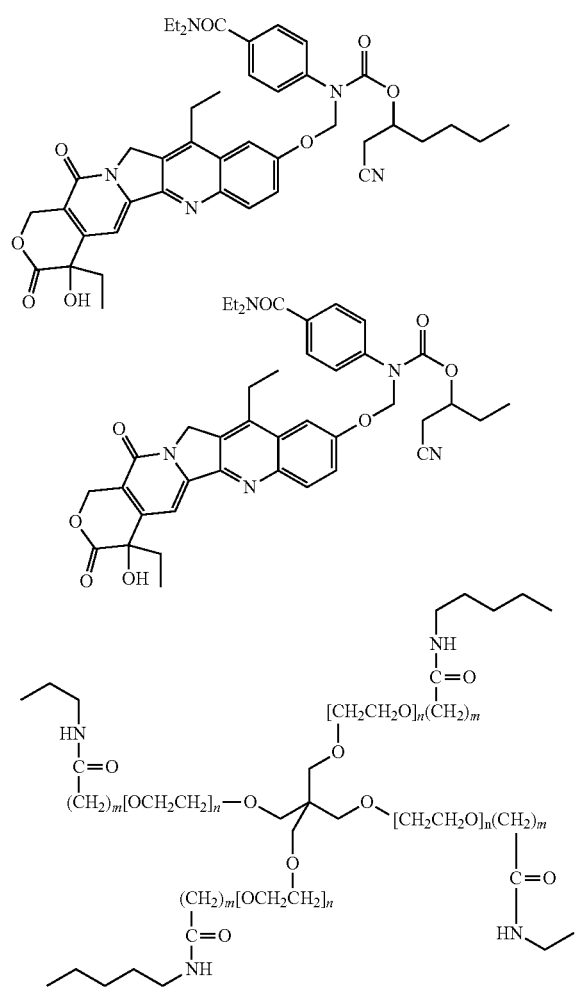
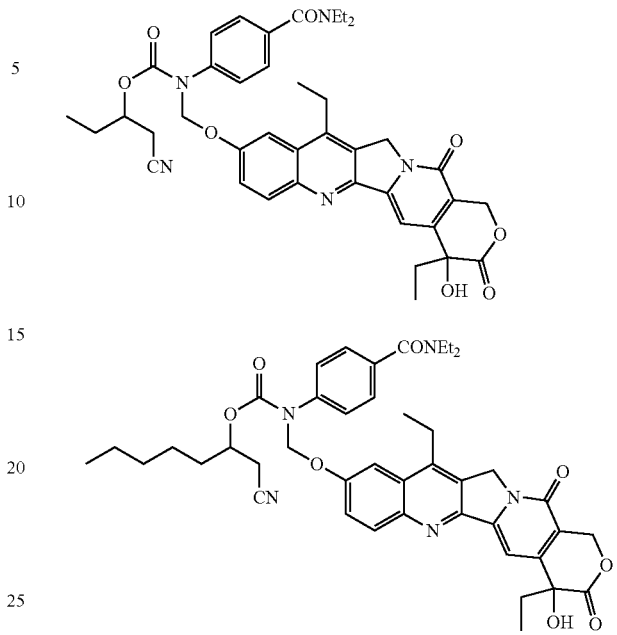
wherein m = 1-6 and n is 200-250.
2. The conjugate of claim 1 wherein m is 1.
3. A pharmaceutical formulation comprising a conjugate of claim 1 together with a pharmaceutically acceptable excipient.
4. The formulation of claim 3, wherein the pH of the formulation is between 4.0 and 6.0.
* * * * *